(12) United States Patent
Inman et al.

(10) Patent No.: US 11,988,583 B2
(45) Date of Patent: May 21, 2024

(54) MEASUREMENT OF A DYNAMIC SYSTEM

(71) Applicant: Lucid Scientific, Inc., Atlanta, GA (US)

(72) Inventors: Samuel Walker Inman, Atlanta, GA (US); Richard Allen Bryan, Atlanta, GA (US); Nicholas Quan, Richmond Hill, GA (US); Daniel Bauen, Stone Mountain, GA (US)

(73) Assignee: Lucid Scientific, Inc., Atlanta, GA (US)

( * ) Notice: Subject to any disclaimer, the term of this patent is extended or adjusted under 35 U.S.C. 154(b) by 396 days.

(21) Appl. No.: 16/556,929

(22) Filed: Aug. 30, 2019

(65) Prior Publication Data

US 2020/0116600 A1    Apr. 16, 2020

Related U.S. Application Data

(60) Provisional application No. 62/725,787, filed on Aug. 31, 2018.

(51) Int. Cl.
  *G01N 1/22* (2006.01)
  *G01N 21/64* (2006.01)

(52) U.S. Cl.
  CPC ....... *G01N 1/2226* (2013.01); *G01N 21/6428* (2013.01); *G01N 21/6452* (2013.01); *G01N 2021/6432* (2013.01)

(58) Field of Classification Search
  CPC ............. G01N 1/2226; G01N 21/6428; G01N 21/6452; G01N 2021/6432
  See application file for complete search history.

(56) References Cited

U.S. PATENT DOCUMENTS

| | | |
|---|---|---|
| 3,714,437 A | 1/1973 | Kinsel |
| 4,198,567 A | 4/1980 | Eneroth et al. |
| 5,329,467 A | 7/1994 | Nagamune et al. |
| 5,345,453 A | 9/1994 | Bayer et al. |

(Continued)

FOREIGN PATENT DOCUMENTS

| | | | |
|---|---|---|---|
| DE | 4405375 A1 | 8/1995 | |
| JP | H07313137 A | 12/1995 | |

(Continued)

OTHER PUBLICATIONS

Caitlin Smith, Guide to Micromanipulators, Labcompare Nov. 14, 2012 (Year: 2012).*

(Continued)

*Primary Examiner* — William H. Beisner
*Assistant Examiner* — Danielle B Henkel
(74) *Attorney, Agent, or Firm* — Occhiuti & Rohlicek LLP

(57) ABSTRACT

A method for performing measurements includes providing relative movement between a receptacle and a cover over a measurement interval comprising multiple non-overlapping time periods. A distance between the receptacle and the cover changes along a first axis over at least a portion of each time period. An apparatus for performing measurements includes a receptacle comprising a substrate and a plurality of wells within the substrate, and a cover. The cover includes: (1) a device configured to engage with the receptacle, (2) a control subsystem configured to provide relative movement between the receptacle and the cover, and (3) a measurement subsystem.

43 Claims, 10 Drawing Sheets

(56) References Cited

U.S. PATENT DOCUMENTS

| | | | |
|---|---|---|---|
| 5,968,340 | A | 10/1999 | Land et al. |
| 6,197,575 | B1 | 3/2001 | Griffith et al. |
| 6,395,555 | B1 | 5/2002 | Wilson et al. |
| 6,526,365 | B1 | 2/2003 | Marino et al. |
| 6,802,957 | B2 | 10/2004 | Jung et al. |
| 6,900,030 | B2 | 5/2005 | Pitner et al. |
| 7,038,192 | B2 | 5/2006 | Lu et al. |
| 7,567,346 | B2 | 7/2009 | Fomitchov et al. |
| 7,796,896 | B2 | 9/2010 | Sikora et al. |
| 8,318,479 | B2 | 11/2012 | Domansky et al. |
| 8,476,846 | B1 | 7/2013 | Ess et al. |
| 8,697,431 | B2 | 4/2014 | Teich et al. |
| 9,075,011 | B2 | 7/2015 | Inman et al. |
| 9,170,255 | B2 | 10/2015 | Teich et al. |
| 9,597,026 | B2 | 3/2017 | Meldrum et al. |
| 2002/0037526 | A1* | 3/2002 | Tashiro ............... C12Q 1/6816 435/6.12 |
| 2003/0186217 | A1 | 10/2003 | Bader |
| 2005/0239197 | A1 | 10/2005 | Katerkamp et al. |
| 2007/0273882 | A1 | 11/2007 | Smith |
| 2008/0014571 | A1* | 1/2008 | Teich ................... B01L 3/5025 435/287.1 |
| 2008/0125977 | A1 | 5/2008 | Anquetil et al. |
| 2008/0267246 | A1 | 10/2008 | Volodin et al. |
| 2009/0109809 | A1 | 4/2009 | Kuroda et al. |
| 2009/0208221 | A1 | 8/2009 | Sasai |
| 2009/0233330 | A1 | 9/2009 | Sachs et al. |
| 2010/0024526 | A1 | 2/2010 | Colvin, Jr. et al. |
| 2010/0227385 | A1* | 9/2010 | Teich ................... B01L 3/5085 435/287.1 |
| 2010/0235117 | A1 | 9/2010 | Melnyk et al. |
| 2011/0024620 | A1 | 2/2011 | Hidalgo et al. |
| 2011/0191917 | A1* | 8/2011 | Abramovitch ....... G01Q 10/065 850/1 |
| 2012/0301913 | A1 | 11/2012 | Youngbull et al. |
| 2013/0238145 | A1 | 9/2013 | Hammer et al. |
| 2016/0077083 | A1 | 3/2016 | Teich et al. |
| 2016/0310943 | A1 | 10/2016 | Woizenko et al. |
| 2017/0037355 | A1 | 2/2017 | Barlet et al. |
| 2017/0100715 | A1 | 4/2017 | Cherubini et al. |

FOREIGN PATENT DOCUMENTS

| | | | |
|---|---|---|---|
| JP | 2001513756 | A | 9/2001 |
| JP | 2005516596 | A | 6/2005 |
| JP | 2007530916 | A | 11/2007 |
| JP | 2009180730 | A | 8/2009 |
| JP | 2012108129 | A | 6/2012 |
| JP | 6020513 | B2 | 11/2016 |
| WO | 9923476 | A1 | 5/1999 |

OTHER PUBLICATIONS

Chen et al."Fluorescence Lifetime-Resolved Imaging," Photosynth Res. (2009) 102: 143-155.

Colyer et al., "A Novel Fluorescence Lifetime Imaging System That Optimizes Photon Efficiency," Microscopy Research and Technique71: 201-213 (2008).

Feddersen et al., "Digital Parallel Acquisition in Frequency Domain Fluorimetry," Rev. Sci. Instrum. 60 (9)Sep. 1989.

Ljung, "System Identification: Theory for the User." Prentice-Hall Information and System Sciences Series. Pearson Education Canada, 1987pp. 408-428.

Malachowski, et al., "Analytic Solutions to Modelling Exponential and Harmonic Functions Using Chebyshev Polynomials: Fitting Frequency-Domain Lifetime Images with Photobleaching," Journal of Microscopy, 228(3); 282-2952008.

Müller et al., "Double-Pulse Fluorescence Lifetime Imaging in Confocal Microscopy," Journal of Microscopy, 177(2): 171-1791995.

Piston et al., "Wide-Band Acousto-Optic Light Modulator for Frequency Domain Fluorometry and Phosphorimetry," Rev. Sci. Instrum. 60 (8)Aug. 1989.

Sauer et al., "Time-Resolved Identification of Individual Mononucleotide Molecules in Aqueous Solution with Pulsed Semiconductor Lasers," Bioimaging6 (1998) 14-24.

Squire et al., "Multiple Frequency Fluorescence Lifetime Imaging Microscopy," Journal of Microscopy, 197(2): 136-1492000.

Verkman et al., "Construction and Evaluation of a Frequency-Domain Epifluorescence Microscope for Lifetime and Anisotropy Decay Measurements in Subcellular Domains," Biophysical Chemistry40 (1991) 117-125.

Watkins et al., "A Parallel Multiharmonic Frequency-Domain Fluorometer for Measuring Excited-State Decay Kinetics Following One-, Two, or Three-Photon Excitation," Anal. Chem. 1998, 703384-3396.

Domansky et al., "Perfused Multiwell Plate for 3D Liver Tissue Engineering," Lab Chip, 2010, 1051-58.

Nishimura et al., "Expansion of Intensity Correlation Spectroscopy for Lifetime Measurements—Application to Intracellular Oxygen Dynamics Measurements," Journal of Biomedical Optics, 2007vol. 12(2).

Shin et al., "Cost-Effective Oxygen Gas Sensor via Fluorescence Quenching," Multi-Disciplinary Senior Design Conference2009.

International Search Report and Written Opinion, PCT Application No. PCT/US2019/049044, dated Nov. 25, 2019 (16 pages).

Mozayan et al., "A Novel Biocompatible Biomaterial for On-Demand Generation of Three-Dimensional Oxygen Gradients in Vitro," Transducers 2015, International Conference on Solid-State Sensors, Actuators and Microsystems, Jun. 21, 2015, pp. 1593-1596.

S.C. Land et al., "The Self-Referencing Oxygen-Selective Microelectrode: Detection of Transmembrane Oxygen Flux from Single Cells," The Journal of Experimental Biology, 202: 211-218 (1999).

Kumar et al. "Nerve Injury Induces a Rapid Efflux of Nitric Oxide (NO) Detected with a Novel NO Microsensor," The Journal of Neuroscience, 21(1): 215-220 Jan. 1, 2001.

Mamchaoui Kamel and Georges Saumon, "A Method for Measuring the Oxygen Consumption of Intact Cell Monolayers," Am. J. Physiol. Lung Cell Mol. Physiol. 278: L858-L863 (2000).

Buck et al., "Co-Regulation of Primary Mouse Hepatocyte Viability and Function by Oxygen and Matrix," Biotechnology and Bioengineering, vol. 111, No. 5:1018-1027 (2014).

Gerencser et al., "Quantitative Microplate-Based Respirometry with Correction for Oxygen Diffusion," Anal. Chem. 81: 6868-6878 (2009).

Pettersen et al., "Pericellular Oxygen Depletion During Ordinary Tissue Culturing, Measured with Oxygen Microsensors," Cell Prolif. 38:257-267 (2005).

Daniele Fanelli, "How Many Scientists Fabricate and Falsify Research? A Systematic Review and Meta-Analysis of Survey Data," PLOS ONE 4(5): 1-11 [retrieved from the internet Jan. 6, 2020: https://journals.plos.org/plosone/article?id=10.1371/journal.pone.0005738].

Arain S et al: "Gas Sensing in Microplates with Optodes: Influence of Oxygen Exchange Between Sample, Air, and Plate Material", Biotechnology and Bioengineering, vol. 90, No. 3, XP071152819, ISSN: 0006-3592, DOI: 10.1002/BIT.20348.

Jorgenson R et al: "96-channel microplate surface plasmon resonance fiber optic sensor system "Proceedings of SPIE, vol. 3603, Jan. 23, 1999, XP055418064, DOI: 10.1117/12.346756.

* cited by examiner

MEASUREMENT OF A DYNAMIC SYSTEM

CROSS-REFERENCE TO RELATED APPLICATIONS

This application claims the benefit of U.S. Provisional Application No. 62/725,787, filed on Aug. 31, 2018, which is incorporated herein by reference in its entirety.

BACKGROUND

Various techniques are used to measure oxygen consumption by cells. Some techniques are open-air techniques that measure prepared cells (e.g., intact monolayers of cultured cells). Some techniques are able to perform measurements of cells in vivo. Some techniques are able to perform measurements of cells in a multi-well plate (e.g., cells in wells of a microtiter plate). In some techniques a probe is used to take measurements between two distinct locations within a gradient in order to estimate flux (e.g., using a self-referencing microsensor).

SUMMARY

At least some aspects address a need to measure oxygen consumption of a biological sample on an ongoing basis (e.g., days or weeks) while maintaining a sterile environment for the sample, maintain the sample (e.g., a surface of a fluid containing the sample) in gas contact with an environment, and minimally disruption an oxygen concentration gradient in the fluid. In at least some embodiments, the system comprises a sterile, disposable probe lid attached beneath a durable handheld electronic array of optoelectronic sensors. The probe lid and electronic sensor array are positioned on top of a standard multi-well tissue culture plate. Optical probes integrated within and extending vertically from the disposable lid are inserted into the fluid of multiple tissue wells. The system is designed to avoid hindering overall transport of oxygen to the cells and to minimally disrupt oxygen concentration gradients. The lid is sterile, and the system can reside within an incubator. As such, the system is ideally suited for continual use during a cell culture experiment, lasting up to several weeks. The system is also ideally suited for measuring a response of cells to a treatment (e.g., measuring a change in oxygen consummation after addition of a drug).

In one aspect, in general, an apparatus is used for measurement of a molecule levels (e.g., concentration, rate of consumption or production) in fluid in a receptacle. The apparatus including a device configured to be attached as part of a cover over a receptacle, which has a set of one or more wells each for holding a biological sample immersed in fluid. The device includes a plurality of optoelectronic sensors arranged to acquire optical signals from probes immersed in the fluid. These optical signals represent a molecule level in the fluid at a sensor of the probe. The device also includes a set of one or more actuators configurable to adjust a relative position of the device and the receptacle. Control circuitry in the device is used to control the set of actuators to vary the relative position of the device and the receptacle, and to acquire the optical signals at a plurality of relative positions.

An advantage of the device forming part of the cover over the receptacle is that the device is portable with the receptacle (e.g., a receptacle covered with the device is "handheld" and can be easily moved from one location to another, placed on an incubator shelf, etc.).

Aspects can include one or more of the following features.

There are a plurality of actuators that are jointly controllable by the control circuitry to control an orientation of a plane defined by the sensors of the probes relative to a plane defined by the set of wells of the receptacle. An advantage of this feature is that each sensor can be kept at the same height above the well floor and/or at the same depth in the fluid as each other sensor.

The control circuitry is configured to maintain a relative orientation of a plane defined by the sensors of the probes and a plane defined by the set of wells of the receptacle to be parallel.

The varying of the relative position of the device and the receptacle is over range of motion. In some examples, this range of motion is between 10 micrometers and 3 millimeters.

In another aspect, in general an apparatus includes a lid, or an apparatus set forth above further comprises a lid, configured to be attached to the device to form the cover. The lid has a surface configured to cover the wells of the receptacle (i.e., when the combination of the device and the lid cover the receptacle). The lid also includes the set of probes, such that each probe extends substantially perpendicularly from the surface of the lid.

The lid is configured such that a location of each probe of the lid corresponds to a location of an optoelectronic sensor of the device such that, when the lid is attached to the device, an optical path is formed between a sensor of the probe and a corresponding optoelectronic sensor. For example, the lid is configured such that the location of each probe of the lid corresponds to a position within a well of the set of wells of the receptacle.

The lid is fixidly attached to the device maintaining alignment of the probes of the lid and the optoelectronic sensors of the device. That is, the device is fastened, attached, or placed so as to be firm and not readily movable relative to the lid and its probes.

The lid comprises a sterile material. For example, the lid is configured to, when attached to a receptacle, separate surfaces of the device from the wells, thereby maintaining a sterile environment in the wells. An advantage of using such a separate lid from the device is that the device does not have to be maintained to be sterile without substantial risk of contamination of the biological samples in the wells.

The lid is configured to cover the wells maintaining gas path between the wells and an environment outside the apparatus without forming any straight-line path from in or above any well to the environment. In this way, the environment provides a reservoir of the molecule.

The lid comprises a flexure portion in vicinity of the periphery of the lid, the flexure portion having greater flexibility than other portions of the lid such that in movement of the device relative to the receptacle, at least a first portion of the lid remains in contact with the receptable and at least a second portion of the lid, separated from the first portion by the flexure portion, remains in contact with the device.

The cover formed from the device and the lid is configured to be removable from the receptacle without moving the receptacle.

The apparatus of any of the preceding claims wherein the device has a mass of less than 1000 grams, or a mass of less than 250 grams.

The set of flexure portions form a spring having a force such that a weight of the device is sufficient to compress the flexure portions over the varying relative position of the device and the receptacle, and the spring applies sufficient force to maintain contact of the lid with the device (i.e., maintains the lid fixedly attached to the device) over the varying relative position.

The device includes guide elements for engaging with corresponding elements of the lid to fix a relative position of the lid and the device. For example, the guide elements include at least one of a protrusion and an indentation in a surface of the device. As another example, the guide elements include a magnet for mating with a magnet in the lid.

The device includes a data interface for receiving data from a corresponding element in the lid. For example, the data interface comprises electric contacts for electrically connecting to corresponding electrical contacts of the corresponding element of the lid. As another example, the data interface comprises an imaging sensor for acquiring an image of a portion of a surface of the lid. As yet another example, the data interface comprises a radio frequency communication device.

The data interface is coupled to the control circuitry for controlling the actuators and acquisition of the optical signals from the sensors.

The apparatus further comprises the receptacle.

The lid is attached to the device and disposed between the device and the receptacle maintaining a sterile barrier between the surface of the fluid and the environment (e.g., such that there is no straight gas path from a surface of the fluid and an environment outside the apparatus) and there is at least some gas path between each well and the environment.

The receptacle comprises a plurality of wells, and the lid is configured with at least one probe corresponding to each well. Alternatively, the receptacle has a single well, and the lid is configured with multiple probes corresponding to the single well.

The apparatus further comprises a data processing system configured to accept data representing sensor values acquired at multiple relative positions.

The data processing system is configured to combine the accepted data to compute a consumption rate of the molecule by the biological sample.

The data processing system comprises a display for displaying quantities derived from the sensor values. For example, the data processing system is configured to display the quantities derived from the sensor values in combination with reference quantities.

The molecule comprises oxygen.

In another aspect, in general, a lid of any type described above is configured for use with a device and a receptacle. A separate lid has an advantage that it can provide a cost effective consumable portion of the apparatus that can be provided separately from the device, which is reused from experiment to experiment. Furthermore, different types of lids (e.g., interchangeable lids), for example, with different sensors, may be used to measure levels of different molecules.

In another aspect, in general, a method for measuring a molecule levels in fluid in a receptacle makes use of any apparatus set forth above. The method includes causing adjustment of the relative position of the device and the receptacle, including moving the sensors in the fluid without substantial disruption of a gradient of a level of the molecule in the fluid while maintaining a gas path from the wells of the receptacle and an environment outside the apparatus. Sensor signals are acquired at a plurality of the relative positions (e.g., at various locations in the gradient field of the level of the molecule). Data determined from the acquired signals is communicated from the device to a data processing system separate from the device.

In another aspect, in general, a method for performing measurements includes providing relative movement between a receptacle and a set of probes over a measurement interval comprising multiple time periods (e.g., distinct non-overlapping parts of the measurement interval). A distance between the receptacle and the probes changes along a first axis over at least a portion of each time period. The receptacle comprises a set of wells (e.g., a plurality of wells). At least one well (e.g., each wells) supports a sample and containing a fluid, the fluid having a top surface exposed to a gas, and the gas having a concentration of a molecule, where the sample consumes or otherwise interacts with the molecule within the fluid. Each probe configured to measure a concentration of the molecule within the fluid, at a distance from the bottom surface of a well that depends on the distance between the receptacle and the probe. The relative movement is along an axis substantially perpendicular to the plane of the top surface of the fluid. The method also includes acquiring measurement data from the set of probes, over each of a plurality of the time periods. For at least a first probe configured to measure a concentration of the molecule within the fluid contained in a first well of the set of wells: measurement data acquired from the first probe includes at least two data samples acquired at different respective distances from the bottom surface of the first well within a first time period of the plurality of the time periods, a maximum elapsed time between consecutive data samples acquired within the first time period is less than a predetermined threshold, for example, based at least in part on a time constant associated with a square of the difference between the respective distances at which the consecutive data samples were acquired, a square of the characteristic length (e.g., diameter of the cross-section of the probe parallel to the fluid surface), and/or on a diffusion constant associated with flow of the molecule within the fluid.

In some embodiments, the first well is deep enough to provide at least 10 microns between the bottom surface and the top surface of the fluid in the first well.

In another aspect, in general, an apparatus for performing measurements includes a receptacle comprising a substrate and a set of wells (e.g., a plurality of wells) within the substrate (e.g., a "well plate" or a "multiwell plate"), and a cover. The cover includes a lid and a device. The lid is configured to engage with the receptacle. The lid includes a set of probes each extending from a surface of the lid into a corresponding well of the set of wells, with the lid being substantially fixedly attached to the device to maintain the locations of the probes on the lid relative to the device, and shaped to maintaining a sterile barrier between the wells and the environment (e.g., forming only tortuous paths and avoiding any straight path between any portion of the air gap over the wells and an atmosphere outside of the air gap). A control subsystem configured to provide relative movement between the receptacle and the device, where a distance between the receptacle and the device changes along a first axis based on movement of a plurality of mechanical actuators, and where each of the mechanical actuators is configured to move a moveable element within the device so that the moveable element contacts the receptacle when the device is engaged with the receptacle, and (3) a measurement subsystem configured to provide excitation light propagating from two or more of the plurality of probes and configured to collect emission light propagating into the two or more of the plurality of probes.

In some embodiments, the moveable element comprises a flexible membrane.

In some embodiments the device has a small form factor and has low power consumption. A small form factor, ideally as small as 127.8×85.5~mm (i.e., the footprint of some receptacles) and low mass (e.g., less than roughly 250 grams, or less than 1000 grams), enables the device to sit on top of such a plastic receptacle and to be a hand held device. A small form factor is achieved using methods contained herein. Finally, the device uses less than two and a half watts, or ideally less than half a watt of power on average, or more ideally less than 0.1 watts, enabling the entire device to be powered by USB and allows it to reside inside an incubator (i.e., an enclosed temperature and humidity controlled environment) without an appreciable increase in temperature of the environment.

Aspects can have one or more of the following advantages.

The techniques and systems described herein can be used to measure consumption or production of a compound with a fluid-containing well of the receptacle. In where oxygen is consumed by cells a gradient forms between the top surface of the fluid, where the oxygen concentration is in equilibrium with the environment (i.e., a gas reservoir of the compound, e.g., oxygen), and the cells, where the concentration of oxygen is lower than saturation due to consumption. At steady state, oxygen consumption is proportional to the concentration gradient and the oxygen diffusion constant. Thus, oxygen concentration within the well can be measured and converted to a cellular oxygen consumption rate. In some embodiments of the system, an array of small-diameter oxygen probes are inserted into wells and move vertically (normal to the plane of the well bottom) in a pattern. Oxygen concentration can be read throughout this movement pattern. Although probe movement may disrupt the concentration gradient and the system does not necessarily ever reach perfect steady state, these concentration measurements can be used as inputs to an algorithm to produce a time series of values corresponding to cellular oxygen consumption, a strong indicator of metabolic activity. Using the readings, several other system properties can be inferred including, for example, measurement of equilibration of a compound within a fluid-containing well of the receptacle, or the spatial distribution of the underlying cells. This measurement technique offers significant advantages over conventional techniques in terms of accuracy, minimal disturbance to the cells, and measurement robustness.

Other features and advantages of the invention are apparent from the following description, and from the claims.

DESCRIPTION

1 Overview

Various embodiments of a measurement system, which includes a measurement unit and associated computing and control circuitry for controlling and receiving data from the measurement unit (some of which may be included within and/or coupled to the measurement unit), are used for measuring oxygen consumed or produced by cultured cells, or for measuring oxygen equilibration with a surrounding environment. The system can provide non-invasive, continuous, real-time oxygen consumption measurements. It is useful, for example, for measuring oxygen consumption when there is little or no fluid convection. Furthermore, it is suited for measurements when cells are cultured in an open well format, where the primary source of oxygen delivery into the fluid is across the air-liquid interface at the top of the well. Still further, it is useful when cells are mammalian cells, and when cells are adherent to the bottom of the culture well. In different embodiments, different aspects of the system may be adapted for any of a wide variety of culture form factors.

Figure 1A:
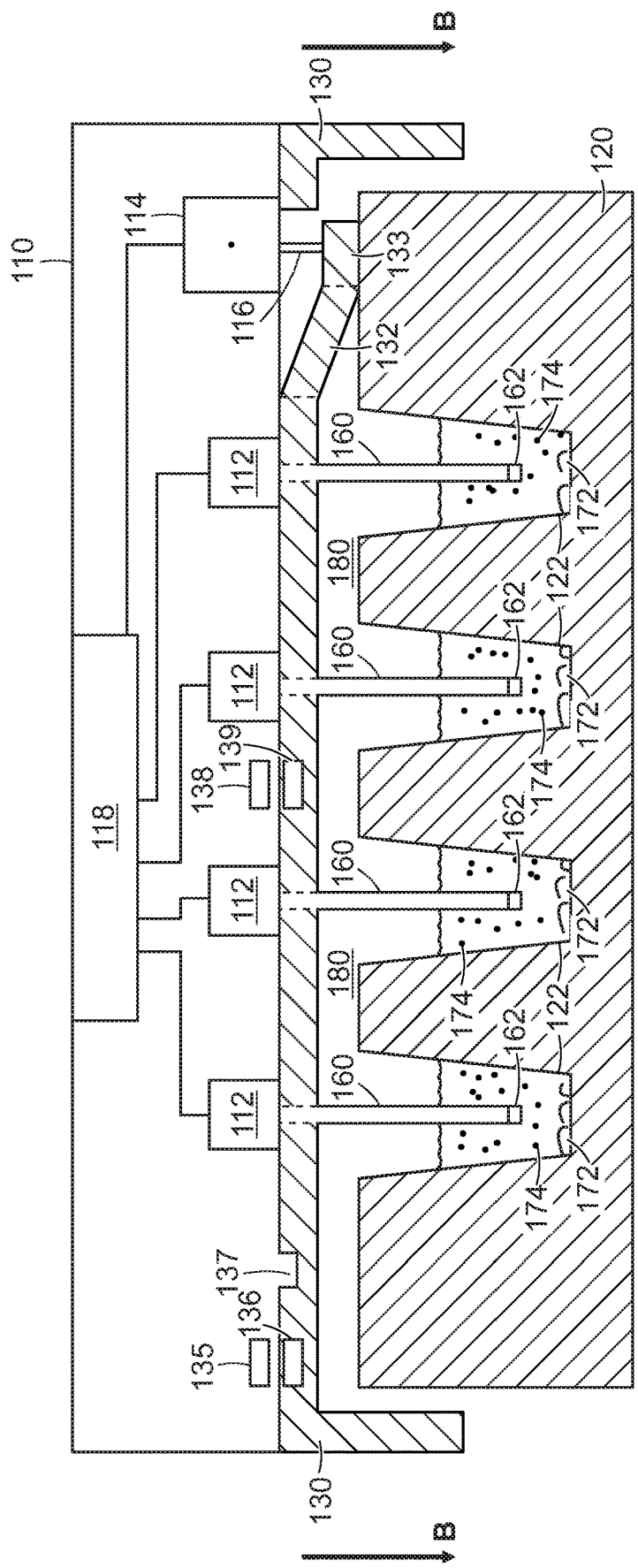
FIGS. 1A-B are cross-sections of an example measurement unit.
Figure 1B:
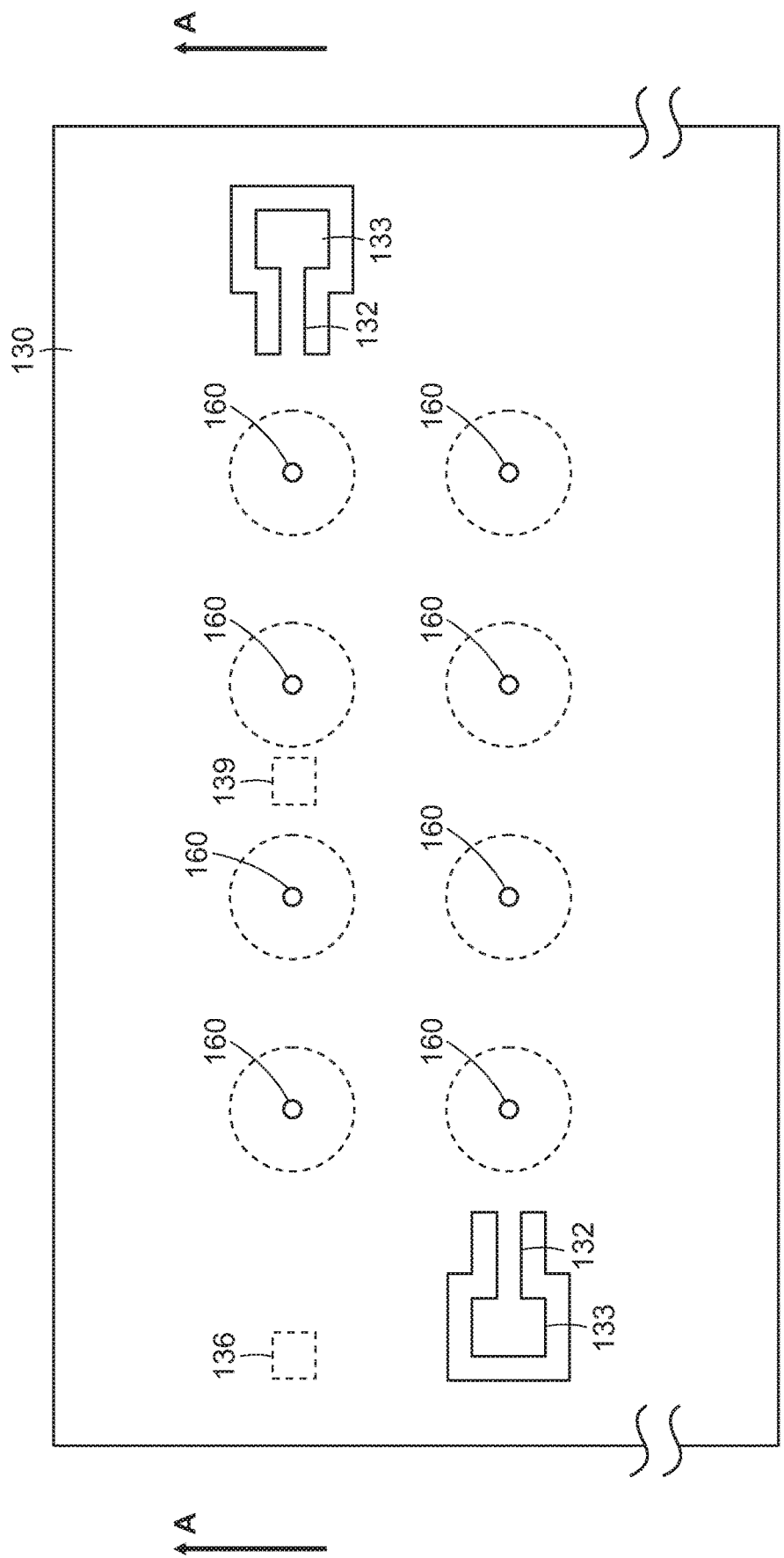

Referring to FIGS. 1A-B, an example measurement system includes a measurement unit 100 that comprises a sterile, disposable (e.g., consumable) probe lid 130 attached beneath a durable (e.g., non-consumable) device 110 supporting an array of optoelectronic sensors 112. FIG. 1A is a cross-section looking horizontally at point A illustrated in FIG. 1B, and FIG. 1B is a cross-section at a point B illustrated in FIG. 1A. The probe lid 130 and array of optoelectronic sensor 112 are positioned on top of a culture plate 120 (also referred to as a "receptacle"). The device 110 and lid 130 together are also called the "cover," with the lid being a surface coupled to the device and covering the culture plate 120, which includes multiple wells 122. Optical probes 160 are integrated within and extending vertically from the inner surface of the disposable lid 130 are inserted into the fluid 174 of the tissue wells 122. For example, the probes are integral and molded of the same material as the remainder of the lid, while in some examples, the probes include light guides made of a different material and molded into the remainder of the lid. As described further below, each of the probes 160 includes a probe tip 162, which is immersed in the liquid 174 and which converts a property such as oxygen concentration into an optical emission, which is passed via the corresponding probe to the optoelectronic sensor 112 in the device 110 (e.g., in response to an optical signal emitted from the sensor 112 that excites the probe tip 162). Circuitry 118 in the device then stores and/or communicates the measurements to an external processing system. Also as described further below, the device includes electrically controlled actuators 114 (only one of which is illustrated in the cross-section of FIG. 1A), which can change of separation of the device 110 and the plate 120, for example, by extending separator pins 116 that push against the top surface of the plate 120 through the lid 130, thereby control change of location of the probe tips 162 within the wells 122.

The system can also contain a control and data storage hub which interfaces the device 110, for example, via the circuitry 118. This interface can be wireless or wired. The control hub can interface multiple measurement units simultaneously. Additionally, the control hub can provide an interface for remotely accessing data, and it can host a visualization of the data. The data can also be visualized in real-time through a remote machine that is accessing the data through the hub or through another remote machine that is relaying the data collected by the hub.

The example system is designed to avoid hindering overall transport of oxygen to the cells and to minimally disrupt oxygen concentration gradients. The lid is sterile, and the measurement unit resides within an incubator. As such, the example system is ideally suited for continual use during a cell culture experiment, lasting up to several weeks.

Within a well, when oxygen is delivered to the fluid primarily at the air interface and cells at the bottom or suspended within the well consume oxygen, a gradient of oxygen concentration forms between the oxygen saturated fluid at the top of the well and the fluid with reduced oxygen concentrations at the bottom of the well (or at the position(s) of the cells within the well). Alternatively, cells within the well might produce or consume another compound that equilibrates with the gas in the air above the well, where it is useful to measure production or consumption of this gas, or to monitor equilibration of the solute contained in the fluid with the surrounding environment. The properties of this gradient reveal local transients of oxygen transport that occur within the well throughout an experiment. These properties are described by Fick's laws and relate directly to oxygen consumption by the cells.

Without intending to be bound by theory, Fick's first law relates diffusive flux to concentration under the assumption of steady state (a valid assumption at infinitesimally small length scales)

$$J = -D \frac{\partial \varphi}{\partial x}$$

where J is diffusive flux, D is the diffusion coefficient, $\varphi$ is the concentration and x is the spatial position. Fick's second law predicts how diffusion causes concentration to change with respect to time t $$\frac{\partial \varphi}{\partial t} = D \frac{\partial^2 \varphi}{\partial x^2}$$

During operation, probes move up and down within the wells (length scale of roughly a millimeter) and the system records oxygen concentrations within the gradient. These concentration readings processed and, coupled with knowledge of the system movement, provides an oxygen consumption readout for the user.

In some embodiments, the system precisely moves probes relative to previous probe positions, but does not provide absolute positioning relative to the position of the fluid surface or the position of the cells. As such, the terms height (relative to the bottom surface of the well) and depth (relative to the fluid surface) are not intended to imply certainty in absolute height or depth relative to an exact position of the physical fluid surface (which can change during an experiment) or the well bottom (which can vary according to variances in manufacturing), but rather an idealized or approximated height or depth relative to reference points in space that correspond to approximate (nominal) positions.

The system's computing subsystem can be configured to perform an estimation algorithm that is based on measurements at relative positions, so it only needs to ensure that the probes reside within the gradient to be measured. In some cases, this a useful improvement over a fixed probe approach, for example, since the system can tolerate absolute positional inaccuracies while providing an accurate readout. These absolute position inaccuracies can arise from many sources including:

Variance in well plate dimensions (e.g. depth, volume, edge heights, etc.)

Variance in fluid volume (e.g. as a result of evaporation, mis-calibrated or inaccurate pipettes, or due to variations in plate volume)

Variances in the manufacturing of various physical components of the system itself, including the actuation components and lid.

There are many commercial benefits that can be exhibited in some embodiments that result from the system's tolerance for absolute positional inaccuracy. These include:

Compatibility with a variety of plates from a variety of different vendors.

Manufacturability at lower cost since it can be produced with lower-tolerance manufacturing processes. For example, low cost injection molding instead of precision-milling for lid production.

Customer ease-of-use. Impacts of evaporation and fluid volume inaccuracies are minimized. Re-calibrations for maintaining absolute positional accuracy are not required.

Longer system life-span. The system is able to tolerate wear in various components that may affect its positional accuracy.

2 Example Measurement Unit

Referring again to FIG. 1, the measurement unit 100 comprises a cell culture plate 120 with an array of open wells 122 containing cells 172 immersed in liquid 174. Resting on top of this plate 120 is a sterile, disposable lid 130 with an array of probes 160 extending vertically from the lid down into the cell culture wells. An oxygen sensitive material is affixed to the tips 162 of these probes, which are contained within the culture fluid 174 of each well 122. An array of optoelectronic sensors 112 in a durable device 110 is coupled to the probe lid 130 (e.g., optically by maintaining the device 110 be contact with the lid 130), and the sensors 112 read oxygen concentration at the probe tips 162 by processing optical emissions from the probe tips 162 which pass via the probes 160 to the sensors 112. The probes 160 are moved up and down within the well in order to measure oxygen concentration at multiple positions. Actuators 114 provide vertical movement of the device 110 relative to the plate 120, and thereby movement of the probe tips 162 relative to the wells 122. The unit 100 connects to a data and power hub which processes, stores and provides access to or displays data collected on the sensors. Various embodiments of different features of the example measurement unit will now be described.

2.1 Durable Device Supporting Sensors and Actuators 2.1.1 Direct Coupling of Optical Sensors and Probes In general, in various embodiments, the probe tips 162 are configured to move vertically up and down relative to the cell culture plate 120. In some embodiments, this relative movement can be accomplished by fixing the probe lid, such as within an enclosure, and oscillating the well plate vertically. In other embodiments, the probe lid can oscillate vertically while the well plate remains stationary. This could occur on the shelf of an incubator, for instance, where the plate remains resting on a shelf, and the probe lid oscillates above the well plate. This latter type of embodiment is described further below.

The probe tips can be configured to be coupled to the optoelectronics. Optical sensors typically employ flexible optical cables to isolate the sensing material on the probe from the optoelectronics. Flexible cables coupling the sensing electronics and probe lid allow the lid to oscillate freely. Alternatively, optical cables are omitted in some optical sensing environments, for example when used with a microscope the optical signal is read directly from the material. This allows the sensor electronics to move freely relative to the probe material—for example with a plate reader. wherein the embodiments described below, an optical fiber is essentially fixidly attached to the optoelectronic sensors of the sensor array in the device such that vertical oscillation of the optoelectronics corresponds directly to vertical oscillation of the probe tips within the wells of the plate.

Direct coupling is advantageous, in some embodiments, because a minimal length stretch of optical fiber or a light pipe can be employed, system complexity and size are reduced, and the number of interfaces where light can be lost is reduced—increasing signal intensity.

2.1.2 Reversible Coupling

The durable device 110, which includes the array of optoelectronic sensors 112, is fixidly attached to the disposable lid 130, This fixed attachment is reversible so the disposable lid 130 can be removed and replaced. In some embodiments, magnets (e.g., 135, 136 shown in FIGS. 1A-B) are used to hold the two parts together, and alignment features in both parts ensure connections are repeatable (e.g., to align the sensors 112 with corresponding probes 160). Alignment features can include, for example, two pins on the device with a corresponding hole and slot in the disposable portion, or a kinematic coupling with three balls on the device and a cup, valley and plane on the disposable portion (e.g., pin 137 in FIGS. 1A-B, which engages with a corresponding valley in the lid 130). Optionally, magnetic retention features can be turned on or off either by using electro magnets, by using opposing permanent magnets that can be aligned or misaligned, or by temporarily turning on an electromagnet to counteract a permanent magnet. Alternatively, a slide lock or some other mechanical mechanism can be used for both holding and aligning the lid to the device.

2.1.3 Electronics and Data Storage

The durable device 110 contains electronic circuitry 110 that assists to process oxygen concentration readings, monitor additional sensor inputs, run decision-making algorithms based on these inputs, provide sampling and actuation instructions, and communicate with a data hub. These additional electronics include microcontrollers for general processing and specialized digital processing devices such as field programmable gate arrays (FPGA) for high speed control and calculations. The electronics also include non-volatile memory for storing device specific information, including calibration variables for the device. These calibration variables can potentially account for variances in electronics including oscillators, amplifiers, gain resistors, capacitors, etc.

Certain optical components are present for each sensor in the array. These components can include at least a portion of a lens, a dichroic mirror, a first surface mirror, an emission filter and an excitation filter. The light emitting device (a light emitting diode LED) and the light sensor (a photodiode) often have integrated lenses.

The device can also include wireless communication features in order to provide data to the data hub. It can further include on-board power storage (e.g. batteries) so that operations can be run continuously in case of disruption to externally supplied power. Back up power also enables a more extensive shut down process. For example, the actuation features can be retracted to a safe position inside the durable device.

2.1.4 Additional Sensors

Optional additional sensors include atmospheric pressure, temperature and humidity sensors, which can be used for calculating local oxygen saturation values. An accelerometer can also be included for monitoring orientation of the device and for checking whether the device is being transported or is stable on an incubator shelf. This information is useful for automated initiation and termination of movement patterns. Temperature sensors can be used to monitor stability of the incubator environment, such as when doors are opened. An ambient light sensor can also be used for this purpose which may be useful in minimizing power consumption. Oxygen, temperature and acceleration sensors can also infer when culture media has been exchanged within the wells. Relative humidity measurements are also useful for general incubator monitoring since low humidity levels increase media evaporation rates.

Patterns and threshold values from sensor readings can automatically trigger the initialization or termination of measurement and or actuation series. In this manner, the device can smartly anticipate user intention and eliminate the need for certain user interface mechanisms like buttons. The acceleration sensor can also be configured to detect movement caused by the actuation features. In this configuration, the acceleration sensor can be used to monitor system performance and can trigger corrective steps if the system is not performing as expected.

2.1.5 Three Point Actuation System

In some embodiments, vertical (i.e., z-axis) motion of the device 110 and lid 130 relative to the plate 120 is accomplished with a single actuator and linear guides such that the actuator maintains a parallel arrangement of the device and the plate, thereby causing a plane through the probe tips to remain parallel to the plate. In a preferred alternative embodiment, vertical position of the probes within the well can be controlled by setting height at three positions in the xy-plane of the device 110 and the fixidly attached lid 130. Although this distributed positioning system is more complex than a configuration employing linear guides and a single actuator, there are benefits to three point actuation in that it allows for a system that is relatively large in the plane normal to the direction of travel and small along the dimension parallel to the direction of travel. The three actuation points can be operated in synchronization with each other to keep the plane of the probe tips parallel to the plate. Alternatively, the actuators may be operated to achieve different separation of the device and the plate at the different actuator points such that tilt of the lid and corresponding plane of the probe tips can be controlled. For example, in such an alternative some probes travel across a greater distance than other probes in the system.

The actuation points can be set within the footprint of standard multi-well plates, where they can press off from a flat surface near the top of wells. Alternatively, cells can be omitted from three of the wells and the device can push off from the well bottoms. The actuation points can also be located outside the footprint of a standard plate and can push off from an incubator shelf, for example, or a specially designed platform which also holds the well plate. Features in the well plate or a specially designed platform can receive the actuation points. These features could be simple dimples or a combination of a dimple/slot/plane could be used as a kinematic coupling for precise placement.

In order to determine the vertical position of the probes given the position of the three actuation points, the xy-coordinate system can be translated such that one of the actuation points resides on the origin and a second point resides on the x-axis.

Each well center is then translated onto the new set of axes. The slope between the first actuation point at the origin and the second actuation point on the new x-axis is then found. Next the slope between the new x-axis and the value of the third actuation point along the new y-axis is found. The z position of each of the well centers is now possible to find using the slopes and coordinates of each well center along the new set of axes.

Figure 2:
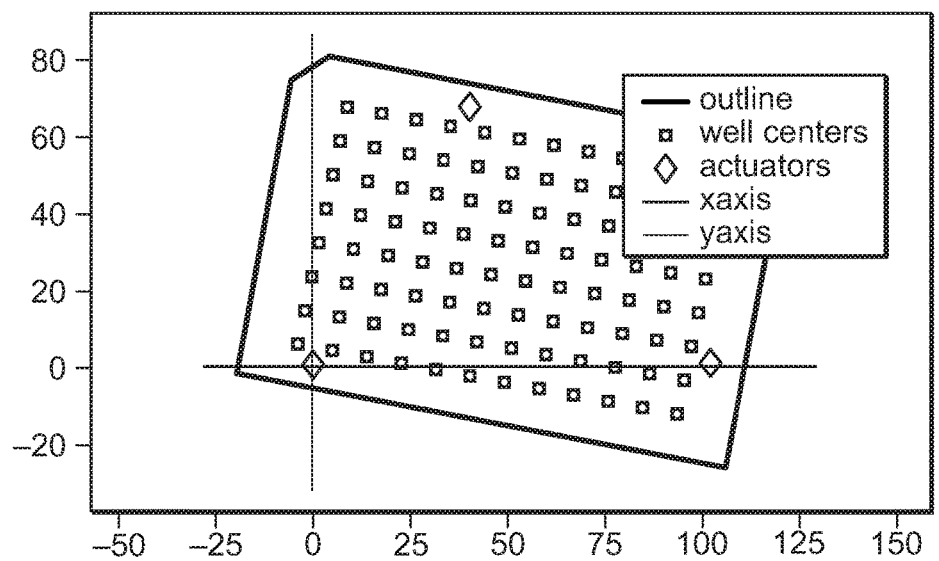
FIG. 2 is a plot illustrating a well coordinate translation.
Figures 3A, 3B, 3C, 3D:
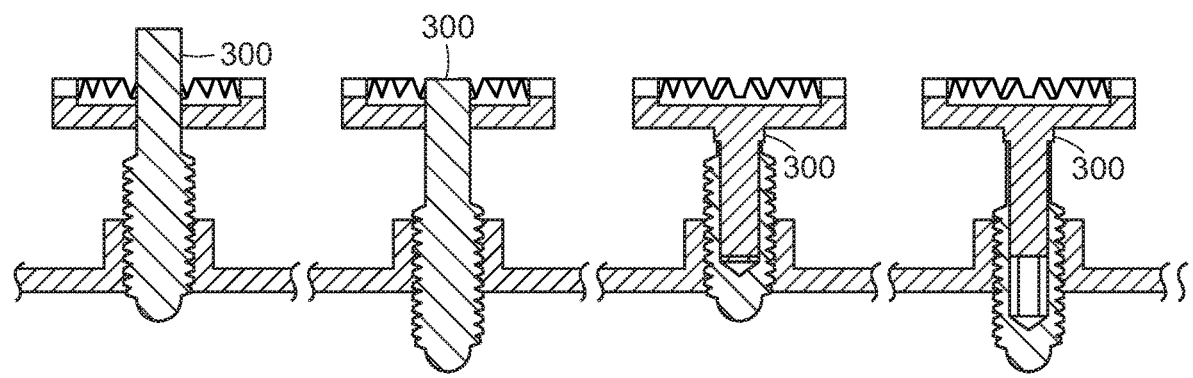
FIGS. 3A-D are cross-sections of an example of telescoping pins.

An image of the translated coordinate system is shown in FIG. 2.

2.1.6 Encoders or Steppers, Limit Switches

Actuators are designed to provide approximate absolute positioning of the probes within the wells and precise positioning relative to previous positions. In one configuration, the actuation points are rods 116 that extend from the durable device 110. Among many potential designs, the rods can be coupled to the durable device through threaded bushings in the actuators 114. When the rods are turned around their cylindrical axis, they extend or retract relative to the device. In another configuration, a disk with an incline abuts the upper end of the pin such that at the thickest portion of the disk, the pin is extended from the device and when the thinnest portion of the disk is aligned with the pin, the pin is allowed to retract into the device. In yet another configuration, flexures are used to translate horizontal motion into vertical motion. In an additional configuration, actuators are held at a fixed height and three lead screws are used to lift or lower the durable portion of the device.

There are multiple options for actuators. Actuation can be provided by piezo devices in combination with position encoders. Alternatively, a DC motor can be used in combination with encoders, or servo motors can be employed. Actuation provided by stepper motors is advantageous because each cycle rotates the stepper motor through a constant angle. Thus, steppers are effective for translation of a precise relative distance.

Stepper motors can integrate with limit switches that can be used on device initialization. Limit switches provide an absolute position reference for the actuators. Additionally, acceleration sensors can be used to assist with determining absolute position, for example orientation of the gravity vector, or by monitoring for missed steps at translation limits by increased or lack of an acceleration signal pattern.

In some embodiments, stepper motors oriented horizontally are coupled with a gear head to increase torque and decrease step size. The gear heads then drive bevel gears which translate the axis of rotation from a horizontal orientation to a vertical orientation. Actuation pins are threaded with a fine pitch and are coupled to matching bushings housed in the durable device. Each step of the stepper motor translates the extension of the pin roughly 1 μm (target translation per step is between 0.01 and 10 μm). Larger step sizes require fewer steps through the full range of travel, which is ideal for power consumption, whereas smaller step sizes allow for smoother operation and increased precision.

Backlash occurs when the direction of movement is reversed. This backlash can be measured and accounted for during operation by adding additional steps each time the direction is reversed. Furthermore, the impact of rotational backlash can be minimized if a lead screw with a fine thread pitch is selected. In this manner, a nominal angular backlash translates to a smaller vertical backlash. The total mechanical advantage of the system for translating stepper steps into vertical positional changes can be maintained by balancing the mechanical advantage gained from a gear box attached to the motor, the ratio of pinion to bevel gear teeth, and the thread pitch of the lead screw. For a given angular backlash, concentrating mechanical advantage to occur at the lead screw can be advantageous in minimizing backlash.

2.1.7 Internally Telescoping Pins

When pins are coupled directly through bevel gears to stepper motors, the position of the bevel gears should remain constant as the pins extend and retract into the device. There are several strategies for allowing the pins to slip relative to the bevel gears. A keyway (or non-circular shape) can be cut into the shaft of the pin and the bevel gear can slip axially along the pin shaft but cannot rotate. In this configuration, as the pin is retracted into the device, the top side of the pin is elevated requiring the device to be large enough to accommodate the pin when it is fully retracted. In some embodiments, the bevel gear is rigidly fixed to a shaft which includes a keyway (or another non circular shape such as a hexagon). This shaft is inserted into another cylindrical shaft with aligning features. The outside of this second shaft is threaded and interfaces with the threaded bushing in the electronic. This format is vertically compact as the bevel shaft telescopes inside the actuation pin. FIGS. 3A-D shows an example embodiment of telescoping pins 300.

2.2 Disposable Probe Lid

2.2.1 Probe Insertion into Wells

The lid 130 includes the array of probes 160, for example with the probes being formed as integral rods that extend from the inner surface of the lid. When the lid is affixed to the device 110, each probe is coupled to a sensor 112 in the sensor array of the device. The lid (or combination of the lid and device) constrains all of the probes such that they move together in a planar fashion. The probes 160 are configured to extend along a vector normal to the plane of the lid (i.e., the horizontal plan parallel to the top of the plate 120). The probes are configured in the x-y plane to align with an array of wells in the well plate 120. The probes can be configured to align with well centers, or other specific positions within the well (e.g., offset from the center, at a fixed distance from the sidewall, etc.), and multiple probes can be configured to cover a pattern within a single well. Alignment of probes in the lid with well plate centers can be achieved with bumps on the inside surface of the vertical portion of the lid that interface tapered outside walls of the well plate. These bumps can be configured as flexures so as to provide flexibility with interfacing plates with tapered walls and plates with a variety of outside dimensions. Probes are configured to penetrate the top surface of fluid in the well and further configured so that some nominal clearance between cells at the bottom of the wells (or suspended within the wells) and probe tips is always maintained. This can be accomplished by positive stops on the surface of the lid that interface with features on the top of the plates so that the probes cannot travel within some nominal distance of the well bottoms (typically 50 to 500 µm, or more preferably 100 to 400 µm). The cross section area of the well normal to the direction of probe travel is substantially constant. The constant cross section minimizes the importance of absolute positioning of the probes within the well.

2.2.2 Lid Provides Vertical Movement Translation

Translation of the lid occurs along the axis of the probes (neglecting any minor tilt of the lid). When cells are uniformly distributed across the cross section of the well, a linear gradient of oxygen can form within the well. Uniform distribution of cells and a substantially constant cross sectional well area are both important aspects of the design of some embodiments because they minimize the importance of absolute position for the probes.

The lid resides on top of the culture plate and promotes a sterile barrier across the top of the culture wells. As such, the non-sterile actuation pins should not directly contact the surface of the culture plate, but (in the case where the actuation pins are contained within the footprint of the plate) should instead contact the lid, which can in turn contact the culture plate. As such, the lid can be configured to include features that enable translation of actuation initiated by circuitry in the durable device to alter the position of the probes relative to the well plates. More specifically, the lid can be configured to enable the optoelectronic sensor array to move the probes vertically within the wells.

Several features of the lid are used to provide this capability. The lid can be configured to contain rigid portions which constrain the probes and interface the durable device and its sensor array. An aspect of the interface between the lid and the sensor array device is that the interface can be configured to constrain the lid such that when the device moves, the lid moves along with it. This constraint is accomplished if, for example, there is a magnetic attraction coupling the lid and device (see Section 2.1.2). Alternatively, this can be accomplished if the lid naturally forces itself to maximally extend away from the well plate, and the device provides enough weight, relative to the strength of the opposing force the lid provides against the well plate, to fully collapse the lid against the well plate. The lid can be configured to also provide flexible or sliding regions which allow translation of motion across the plane of the lid without breaking the sterile barrier.

In the configuration where the lid is reversibly held against the durable sensor array with magnets, the magnets can be arranged or moved between positions such that the holding force can be turned on or off. Alternatively, an electromagnet can be turned on or off, or can be turned on to oppose a permanent magnet.

An alternate configuration could allow the actuation pins to go around the sterile barrier of the lid while staying within the footprint of the plate if a feature of the lid can vertically slide up and down within the lid. When pressed by the actuation pins, these passive pins could in turn press off a horizontal surface of the culture plate.

There are several configurations which allow translation of motion through the plane of the lid while simultaneously maintaining a sterile barrier in the plane of the lid. In one configuration, a flexible membrane is employed. This membrane can be folded or held loosely in place so as to minimize resistance against translation of the actuation pins. A potential drawback to this approach is that a thick membrane may not maintain a constant thickness when pressed by the lid and a thin membrane relative to the thickness of the lid creates a dead space through which the actuation pin can be configured to travel before any movement of the probes occurs relative to the well.

In a second configuration, a pin is provided which can slide vertically within the lid. For maintaining the pin in a vertical orientation, maximizing the vertical distance between the bottom most planar constraint of the lid on the pin and the top most planar constraint of the lid on the pin can be useful. A planar constraint can be for example a bore hole for a cylinder. In some cases, it can be desirable to minimize the thickness of the lid, for example to facilitate injection molding. When thickness of the lid is minimal, the vertically sliding pin can be located in the thin vertical wall of the lid. The vertical travel limits of the pin can be constrained so that the pin remains coupled with the lid. The vertical constraint feature can be composed of two vertically constraining features on the pin and a vertically constraining feature on the lid located between the two constraining features on the pin. Alternatively, the vertical constraint feature can be composed of two constraining features on the lid and a single vertical constraint feature on the pin located between the two vertical constraint features on the lid.

In a third configuration, a flexure is used to allow translation of motion from the durable device and its supported sensor array through the disposable lid plane to the surface of the well plate. The advantages of this configuration include that the movement feature is constrained to the lid within the same plane of the lid (as opposed to along its axis of travel) and the thickness of the flexure along the axis of travel is a fixed value which can be chosen in the design. Specifically, the thickness of the flexure along the axis of travel can be set to minimize dead space. Finally, a flexure can better utilize the available area in the plane of the lid. In some embodiments, the flexures are distributed in vicinity of the periphery of the lid (e.g. as illustrated in FIG. 1B).

2.2.3 Flexure Loading and Neutral Position

When a flexure is used for translating motion through the plate, the flexure can be configured such that the relaxed state of the flexure, the neutral position, falls anywhere inside or outside the limits of travel. Specifically, the neutral position of the flexure can be selected near or beyond the maximum extent of the actuation pin such that the spring action in the flexure does not tend to separate the lid from the durable sensor array.

Figure 4A:
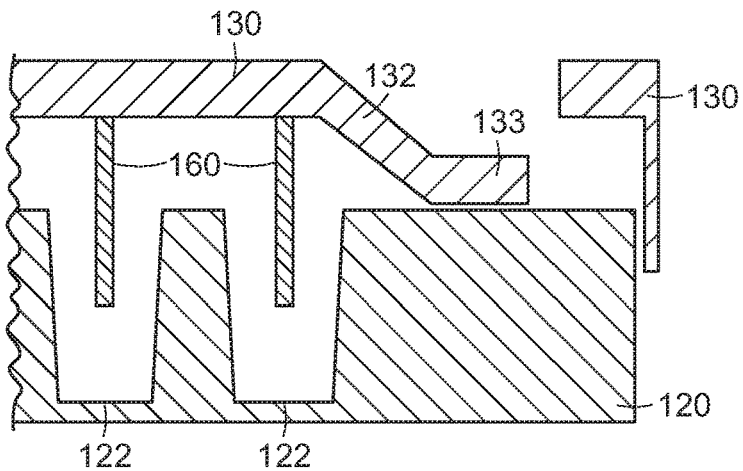
FIGS. 4A-C are cross-sections of an example flexure-based lid between the device and culture plate.
Figure 4B:
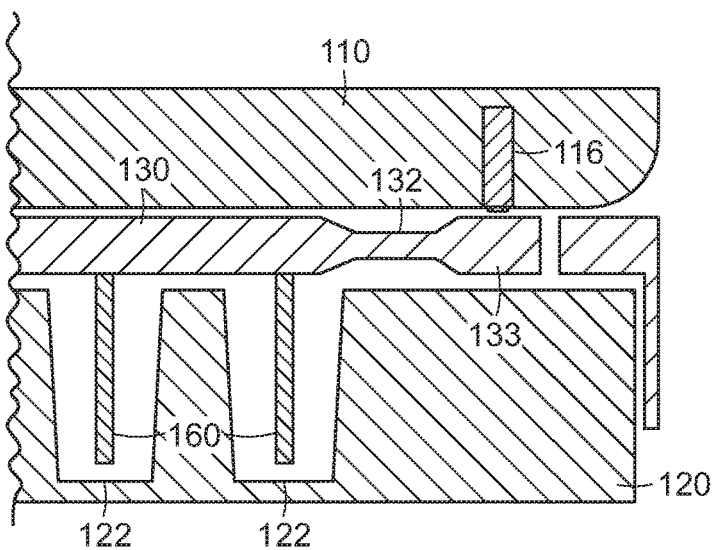
Figure 4C:
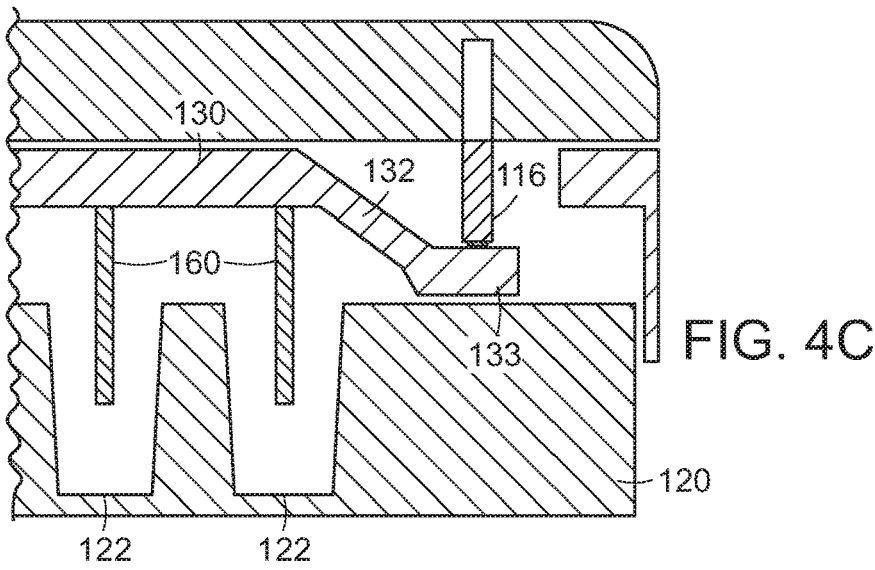

In this configuration, the flexure stiffness is set such that the flexures fully deform under the weight of the handheld sensor array (roughly 250 grams) to where the probes fall to their lowest position within the wells. FIGS. 1A-B show a flexure of the lid where a relatively flexible portion 132 is coupled to a pad 133. Another view is shown in FIGS. 4A-C shows three states of use that demonstrate how the flexures 132, 133 support the weight of the disposable lid when the durable sensor array is not resting on top of the lid (FIG. 4A)

and fully collapse under the weight of the durable sensor array (FIG. 4B). When actuation pins 116 press against the top side of a pad 133 of the flexure, the weight of the sensor array is lifted from the disposable lid and the flexures relax as the lid rises (FIG. 4C). Magnets (e.g., 135, 136 of FIG. 1A-B) or other coupling features can be used to maintain a firm coupling between the lid and the lid reader as the lid rises. The lifting force of the lid flexures also reduces the force from the actuation pins required to lift the sensor array and lid.

The flexure portion 132 in general has greater flexibility than other portions of the lid 130 (e.g. due to material composition or due the geometry of a cut-out of the lind forming the flexure) such that in movement of the device relative to the receptacle, at least a first portion of the lid remains in contact with the receptable and at least a second portion of the lid (e.g., the pad 133 of the flexure), separated from the first portion by the flexure portion, remains in contact with the device.

2.2.4 Flexure Integrated into Lid with Stand-Alone Cover

Figure 5A:
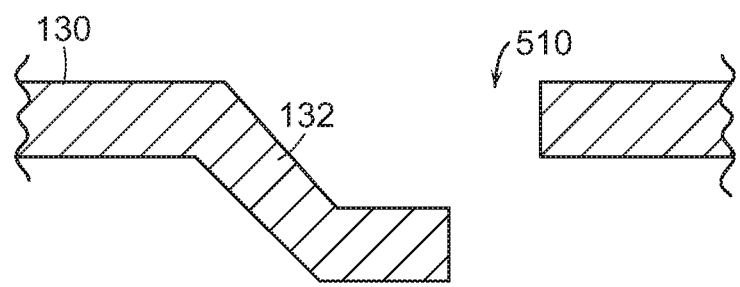
FIGS. 5A-B are a cross-section of an example flexure and flexure cover.
Figure 5B:
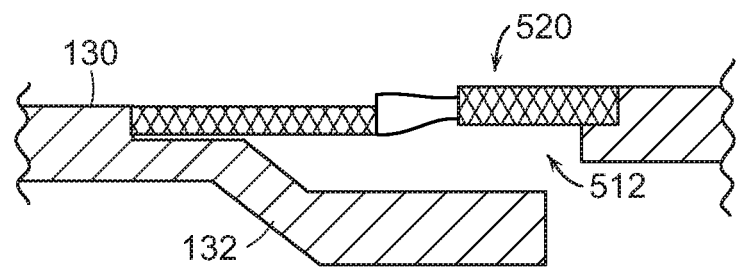

The lid 130 features which allow translation may require gaps in the plane of the lid surface, but these gaps may reduce the sterile barrier formed by the lid. FIG. 5A shows an example gap 510. A separate cover, 520 shown in FIG. 5B, can be inserted over the flexure such that a tortuous path 512 is created and the sterile barrier is maintained. Use of a separate cover eases the fabrication of the lid. In an alternate configuration, the tortuous path features are directly incorporated in the lid, and the flexure is a stand-alone part that is attached to the lid during assembly.

The cover 520 may be permanently attached to the lid 130 through gluing, solvent bonding, press fitting, ultrasonic welding, or any other technique. In one configuration, the cover is a membrane which maintains the complete sterile barrier.

2.2.5 Lid Translucence

The lid is, in some embodiments, colorless and translucent so that light can pass through the lid for imaging (e.g., to illuminate the sample via the lid for viewing through a transparent bottom of the receptacle). For example, the lid is formed from a translucent or transparent acrylic or a polystyrene. Although the electronics contained in the device are opaque, the device and the contained electronics are easily separated from the lid without hindering the sterile barrier formed by the lid.

2.2.6 Light Focusing Features in Lid

Figure 6:
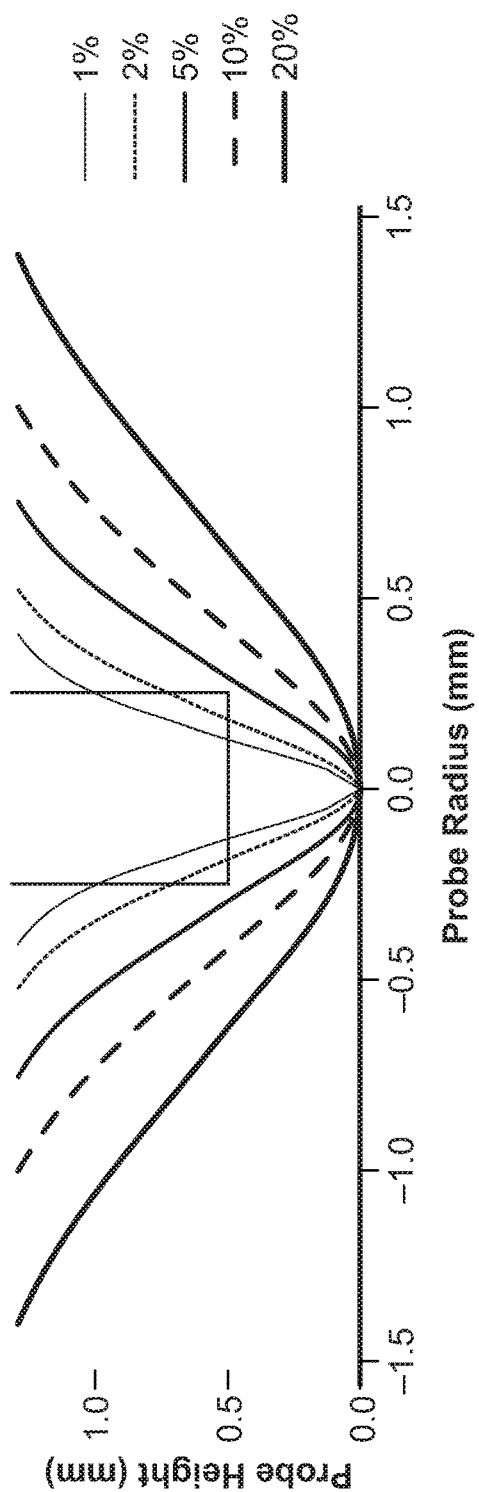
FIG. 6 is a plot illustrating probe envelopes.

The lid, in some embodiments, contains light focusing features that capture light from a large area and focus that light onto a small probe material. The focusing features also collimate or focus light emitted from the sensing material onto the light collection device (e.g., a photodiode). The light focusing and travel feature might include an optical fiber, and the optical fiber might be sheathed in a rigid material, such as a rigid plastic or a stainless steel tube. The end of the light focusing feature that resides in the cell culture well has a minimal diameter, typically between 250 and 800 µm diameter cross section. FIG. 6 shows the amount of disruption to oxygen concentration levels depending on the diameter of a probe held in place at a fixed height within the well. This figure assumes that oxygen consumption by the cells follows a zero order oxygen reaction (i.e., is not substrate limited).

The cross section is minimized so as not to disrupt transport of oxygen to the cells in the well and to minimize disruption of fluid as the probe moves within the well. The shape of the light focusing feature might be cylindrical, or conical, having a larger area for light collection on the top side of the plate, with up to 4 mm or even 6 mm diameter. The probe can optionally be manufactured as a stand alone component then integrated with the lid for example using those techniques mentioned in Section 2.2.4

2.2.7 Integrated Fluid Dispensing Ports

The lid can contain receptacles for holding a small volume of fluid, such as a drug to be applied to the cells in the wells. For example, after a receptacle and cover have equilibrated in an incubator, the fluid can be applied to the samples, and a change in oxygen consumption measured to assess the impact of the fluid on the sample. An array of receptacles can align with the wells of the plate. There are a variety of methods for dispensing the fluid including pneumatic methods for example U.S. Pat. No. 8,318,479, or mechanical methods among others. Furthermore, the design of the receptacle can include multiple flexures that are naturally closed. The number of flexures can be a large number, 4 up to 8 or 16, such that when they are separated, there is a minimal surface area for holding a droplet of fluid. The small volume of fluid can be for example less than a microliter up to 20 or 100 or more microliters. The maximum surface area of any single flexure can be set such that the force of gravity on the drop of fluid is larger than the force from surface tension between the flexure surface and the droplet. The surface tension between the droplet and multiple flexures in the closed position can be larger than the force of gravity on the droplet. The flexures can also include a tab at the top of the receptacle such that, when a pin is inserted into the top of the receptacle, the flexures open allowing any fluid contained in the receptacle to fall into the well below. The tab is, in some embodiments, positioned such that the pin will never contact fluid held in the receptacle. The lowest end of the receptacle flexure can be designed with a point so as to minimize surface tension available for holding fluid suspended.

Another option for integrating fluid dispensing ports is to provide a sloped well that has a shallow slope, where depending on the position of the actuators the slope become steeper dropping the fluid in to mix with the fluid in the receptacle below. In general, a fluid dispensing method that utilizes the movement of the existing system can be used.

2.2.8 Calibration Features

The disposable lid can contain a unique identification code (e.g., embedded in a read-only memory 139 as illustrated in FIGS. 1A-B), which can be read by the durable electronic device 110 either electronically (e.g., with a reader 138 making electrical contact with the memory 139 as shown in FIGS. 1A-B), optically or otherwise. This identification code or process can be used to validate authenticity of the lid. The lid can also contain electronics for storing calibration and usage information, and for validating lid authenticity. The calibration information can potentially include Stern-Volmer constants relating light decay rates to oxygen concentrations, calibration can include information for performing temperature compensation, information for accounting for the useful lifetime of a sensor, and calibration information relating to the response time of the probe and or related diffusion constants.

2.2.9 Integrated Lid Electronics

The lid can contain electronics (for example, an EEPROM) for storing data such as probe calibration constants, identification codes, date of manufacture, and authentication signature. This data can be read by the optoelectronic sensor array through a communication interface. The lid electronics can also contain features for detection of lid attachment and detachment.

3 Example Measurement Process

Figure 7:
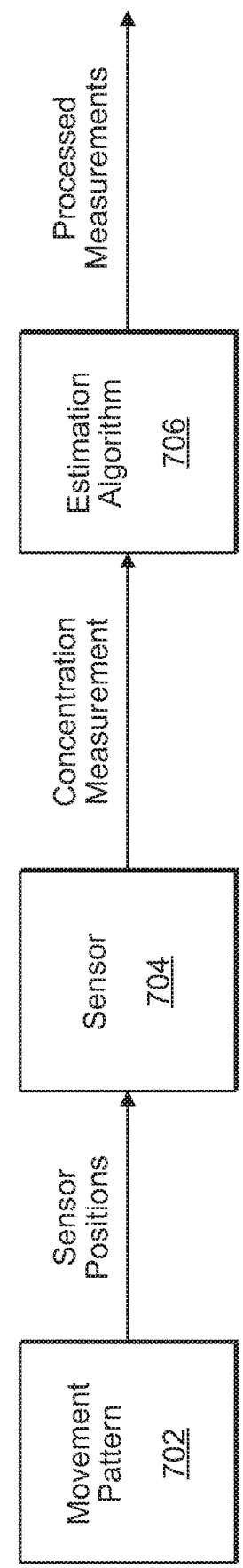
FIG. 7 is a block diagram of an example measurement process.

Referring to FIG. 7, an example of a measurement process 700 that can be used when operating the measurement system includes three different types of procedures, some aspects of which may be performed concurrently: controlling (702) a probe movement pattern, acquiring (704) sensor readings, and executing (706) an algorithm for estimating parameters of the well environment—namely, cellular oxygen consumption.

3.1 Continuous Movement Pattern

In some embodiments, the measurement system moves a set of probes vertically according to a movement pattern. The described pattern is distinct from a pattern configured for taking series of measurements at various fixed heights where the measurements can then be processed such that they correspond one to one with the heights at which they were measured (a step pattern). In a step pattern, movement is configured to pause such that a measurement at a certain height is not correlated with previous heights of the probe (or the more general pattern). In the described system, the movement pattern can be viewed as an input waveform that is transformed by the measurement environment to produce an output signal. When viewed this way, techniques used in signals analysis and processing can be used in characterization and estimation of the measurement environment in order to optimize the measurement process.

One type of movement is continuous movement (e.g., substantially continuous in a time scale of mass transfer in the fluid) in which there are no significant pauses in the movement (e.g., pauses greater than those that may be inherent in use of a stepper motor to control the actuators). Another type of movement is stepped movement in which a probe is moved between two locations relatively quickly and then pauses for a significant amount of time. In some cases, the pause is long enough that a gradient is established. This type of stepped pattern, using "distinct pauses," for which a gradient is at least partially established, is not optimal for some embodiments of the measurement process 700, as the distinct pauses (e.g., longer than about 50 time constants) reduce the responsiveness of the measurement system. A key aspect of some embodiments of the measurement process 700 performed using the described measurement system is that it can operate using movement patterns without the distinct pauses that some other systems may have required in order for the gradient to reestablish and/or the sensor readings to stabilize. Furthermore, while movement speed is variable, it is typically slow enough so as not to exceed a speed limit set by a dimensionless number threshold determined by Stokes flow, and possibly not to exceed a speed limit set by the diffusion constants.

In some embodiments, the movement pattern comprises a "continuous movement pattern." As used herein, "continuous movement" is intended to be understood as either strictly continuous movement (i.e., no pauses), or stepped movement where the duration of the pauses in the stepped movement are relatively short compared to the time constants of the system (e.g., less than about 20 time constants, or less than about 10 time constants). In some instances the system time constant can be based on the diameter of the probe (for example when concerning movement velocity), in other instances the system time constant can be based on the travel distance of the probe (for example when waiting for stabilization relative to a disruption of the gradient by the probe), in other instances the time constant can be based on the distance between the probes and the sample, and in other instances the time constant can be based on the distance between the sample and the air-liquid interface. Such continuous movement can provide continual precise disturbance of the concentration gradient, in a manner that can be modeled without requiring delays for the disturbance to dissipate.

3.1.1 Fixed Movement Patterns

The system can operate with various types of continuous movement patterns. These movement patterns include sinusoids, multiple sinusoids at different frequencies, sawtooth, sinc, chirp, or stochastic/irregular patterns (e.g., a random walk). Generally, patterns that cover a larger range provide a better resolution measurement for a given probe sensor resolution (i.e., are more sensitive to different gradient levels—especially lower/flatter gradient corresponding to low oxygen consumption). On the other hand, patterns that repeat more often (i.e., faster/shorter-period pattern) are able to achieve higher temporal resolution and detect changes in consumption faster. For example, a relatively high frequency, low amplitude (i.e., small movement range) sinusoid pattern responds more rapidly to fast-changing, high gradients, while a slower frequency, larger amplitude pattern gives better accuracy for low (i.e., shallow) gradients at the expense of poorer response time. Additionally, a chirp movement pattern can indicate the response time of a given probe. An irregular pattern can ensure measurement errors are not introduced by an external process that would otherwise interfere due to correlation with a regular pattern.

A known pattern can also be used to filter out noise in sensor readings—yielding an effective gain in sensor sensitivity. For example, if the movement pattern is a sinusoid and the environment is modeled under Fick's law, the signal can be filtered with a low-pass or band-pass filter that attenuates noise while passing the signal resulting from the underlying concentration gradient unaffected. As a waveform, the step pattern occupies a wideband of frequencies and consequently the signal of interest in the sensor readings does as well. Therefore, when using a step pattern, it is difficult to filter out sensor noise without also attenuating the signal of interest.

Since the choice and configuration of the movement pattern results in a tradeoff in system performance, the system can be configured to operate in different modes depending on the type of experiment and the properties of interest to the user. In one configuration, the user may choose a deeper movement pattern (closer to the cells) in order to measure higher-frequency changes in cell behavior. In another configuration, the user may choose a pattern that covers a wider range to achieve better resolution as described above. In another configuration, the user may choose a movement pattern that operates higher in the well to minimize the impact of the probes on oxygen transport to the cells. In another configuration, the user may choose a movement pattern that modulates the oxygen transport to the cells in a specific profile—using the system simultaneously for both measurement and environmental control.

The system can be configured so the user is instructed to select the desired performance from a subset of options or through a short survey, and actual movement patterns are determined based on input from the user. Additionally, ideal movement patterns can be determined automatically as described below.

3.1.2 Dynamic Movement Patterns

In addition to the modes and patterns that can be chosen based on the interests of the user, the system can automatically update movement based on real external events. These different pattern modes can be triggered automatically based on the environmental state as determined by the system's sensors or external sensors. For example, if a low oxygen gradient is detected across most or all wells, the optimal movement pattern may be a deeper one closer to the cells. If steep oxygen gradients are detected across most or all wells, then a movement pattern optimized for higher resolution at steeper gradients could be used. The movement pattern can also be automatically determined based at least in part on determining a direction most in need of additional information (e.g., by using the state of the Kalman filter uncertainties for the wells). Furthermore, the movement pattern can be set independently for each of the actuation points, such that not all probes move along the same vertical pattern. Any number of the following features can be used to implement dynamic movement patterns in some embodiments of the measurement system.

1) The lid contains features, either electrical, active or passive, or non-electrical (eg optical, magnetic), so that the electronics can know when the lid is attached.
2) The electronics have onboard sensors including possibly acceleration, temperature, relative humidity, oxygen partial pressure, ambient light, oxygen, carbon dioxide, or other gas centration, or other sensors.
3) Initiation or termination of movement series can be triggered by lid attachment (detachment) or other sensor readings.
4) Movement pattern contains a zeroing step that utilizes limit switches, potentially triggered by accelerometer/lid attachment.
5) State of the movement pattern (determination of next action) is set not only by the current state of the system (dumb, pre-programmed pattern), but also is adjusted by the state of the environment (system under test) as measured by one or more of the onboard sensors. For example, sensor readings can include any number of the following:
   a. accelerometer readings indicate the plate has been picked up or set down—or is not level on a shelf
   b. across the board low consumption rates trigger the probe to move lower in the well and or with larger ranges, whereas higher consumption rates can trigger the opposite
   c. stability of the gradient can shift the probes to move lower in the wells, can slow the actuation speed, or can increase amplitude
   d. temperature readings below atmospheric (or other environmental factors like humidity) can signal recent change of media, and it might be desirable to keep the probe in a single location

3.2 Sensor Readings

Acquisition of sensor readings to obtain measurements of dissolved oxygen concentration can be performed with a variety methods. A material whose optical properties are sensitive to the surrounding oxygen environment can be used. This material can be excited by light from a LED and the material can return to the ground state through emission of a photon or by transfer of energy to molecular oxygen (quenching). The amount of light emitted and decay rate of light emission are inversely related to oxygen partial pressure through the Stern Volmer relationship. The excitation light source intensity can be modulated between two levels (typically on and off) in an irregular pattern. The irregular pattern can be generated through a pseudo random code, which can be low pass filtered then discretized to two levels. The code can be output by a logic device such as an ASIC or FPGA. The response can be read using an analog to digital converter and the digitized response can be processed on the logic device. Each reading of the light emission signal on the ADC can be processed on the FPGA, for example using a recursive method, and the final system response after some given read time can be further analyzed and converted to a decay rate. Examples of such techniques are described in more detail, for example, in U.S. Pat. No. 9,075,011, incorporated herein by reference (the terminology used in the incorporated document may differ somewhat from that used herein—in the event of a conflict in terminology, that used herein is controlling).

Since the processing is recursive, the read time for the sensor can be set arbitrarily. When the sensor read time is short (1 to 100 ms), each sensor reading might have lower precision relative to longer readings (100 to 600 ms). That is, a longer duration sensor read can be performed for better sensitivity and/or resolution in measurement or a shorter duration sensor read can be performed at the cost of measurement sensitivity and/or resolution. When shorter readings are made, the previous reading for a given sensor can be used to initialize the recursive pattern such that algorithm startup errors are minimized. Multiple short duration readings can be further processed together, forming a single, high precision reading for downstream processing.

This sensor method property can be used to maximize the overall performance of this system. The sensor read time can be changed in coordination with the movement pattern, measurement mode, or experiment type. For example, a movement pattern tuned for better temporal resolution could coincide with use of a shorter sensor read time to yield even better temporal resolution. Alternatively, when maximum sensitivity of the oxygen consumption/gradient measurement is desired, a longer sensor read time could be used in concert with a movement pattern tuned for higher resolution. An alternative configuration could also be to use a longer sensor read time in concert with a smaller range movement pattern in order to satisfy some other system constraint such as cost, size, or power. Similar to the dynamically chosen movement patterns, this tradeoff choice can occur dynamically based on detected environment conditions.

In general, the configurable read time vs resolution tradeoff provided by the sensor reading method provides greater flexibility for the system design and operation.

3.3 Estimation Algorithm

3.3.1 Algorithm Outline

In some embodiments, an example of steps in the algorithm for estimation of parameters of the well environment is as follows:
1) A sensor reading is taken at a timepoint t along the movement cycle.
2) The reading is converted to an oxygen concentration measurement c(t) using calibration data and temperature data.
3) The estimated measurement pattern height is calculated based on the sensor response transfer function and the cycle pattern to produce a concentration measurement as a function of depth c(z, t).
4) Using the new measurement and a set of previous measurements, a regression of concentration vs height is performed and the concentration at one or more discrete pattern heights is interpolated.
5) A Kalman observation is generated based on the interpolated concentration(s).
6) The new observation is applied to the Kalman filter to update estimates according to a state-transition model based on Fick's laws.

Figure 8:
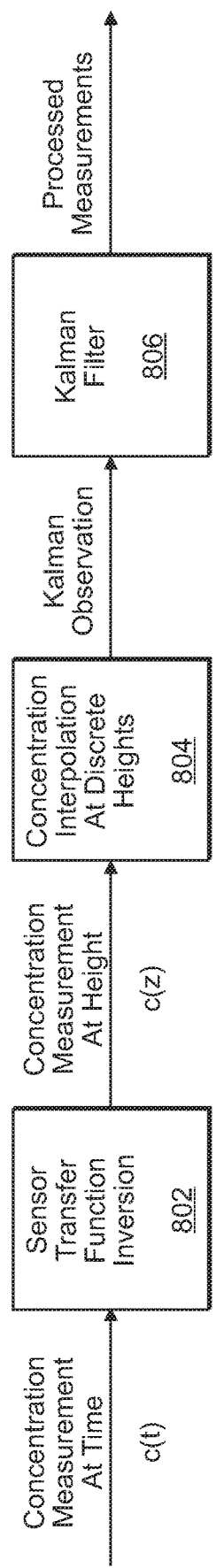
FIG. 8 is a block diagram of an example estimation algorithm.

Referring to FIG. 8, an example of an estimation process that can be used when operating the measurement system includes: receiving a concentration measurement at time c(t) and applying (802) a sensor transfer function inversion to provide a concentration measurement at height c(z, t); performing (804) concentration interpolation at discrete heights to provide a Kalman observation; and applying (806) a Kalman filter to provide processed measurements.

3.3.2 Accounting for Sensor Response

The sensor probes have a response delay that can be accounted for to provide accurate measurement data. One way of accounting for response delay is to pause at a given depth and discard readings until the sensor has had sufficient time to stabilize. This strategy may not be desirable in some embodiments because the consumption rates of cells may be variable, and long fixed pauses reduce transient responsiveness. With a continuous movement pattern, the sensor readings do not necessarily stabilize at a value corresponding to the concentration at the depth where the probes are currently positioned. One approach is to use a movement pattern slow enough relative to the sensor delay such that the readings at a given point within the movement pattern do correspond to the actual concentration at the given depth within some threshold.

Another approach is to consider the sensor response delay as a system transfer function with its input being the movement pattern waveform. This sensor transfer function can be measured or estimated and then compensated for to obtain sensor readings as a function of height. This compensation can entail a time-shift and a scaling depending on movement pattern. For sinusoidal patterns, and assuming an approximately steady-state gradient for a short window of time, the sensor transfer function can be modeled as a low-pass filter which attenuates and phase-shifts the sensor readings. This filtering can then be compensated for by deconvolution (i.e. phase shift and magnitude scaling). This transfer function can be calculated dynamically by assuming a steady state linear gradient or non-steady state gradient (e.g. modeled using an erf function), and then performing a constrained optimization algorithm (e.g. brute force error minimization) to estimate the phase shift (sensor lag).

3.3.3 Observation Model

Figures 11A, 11B:
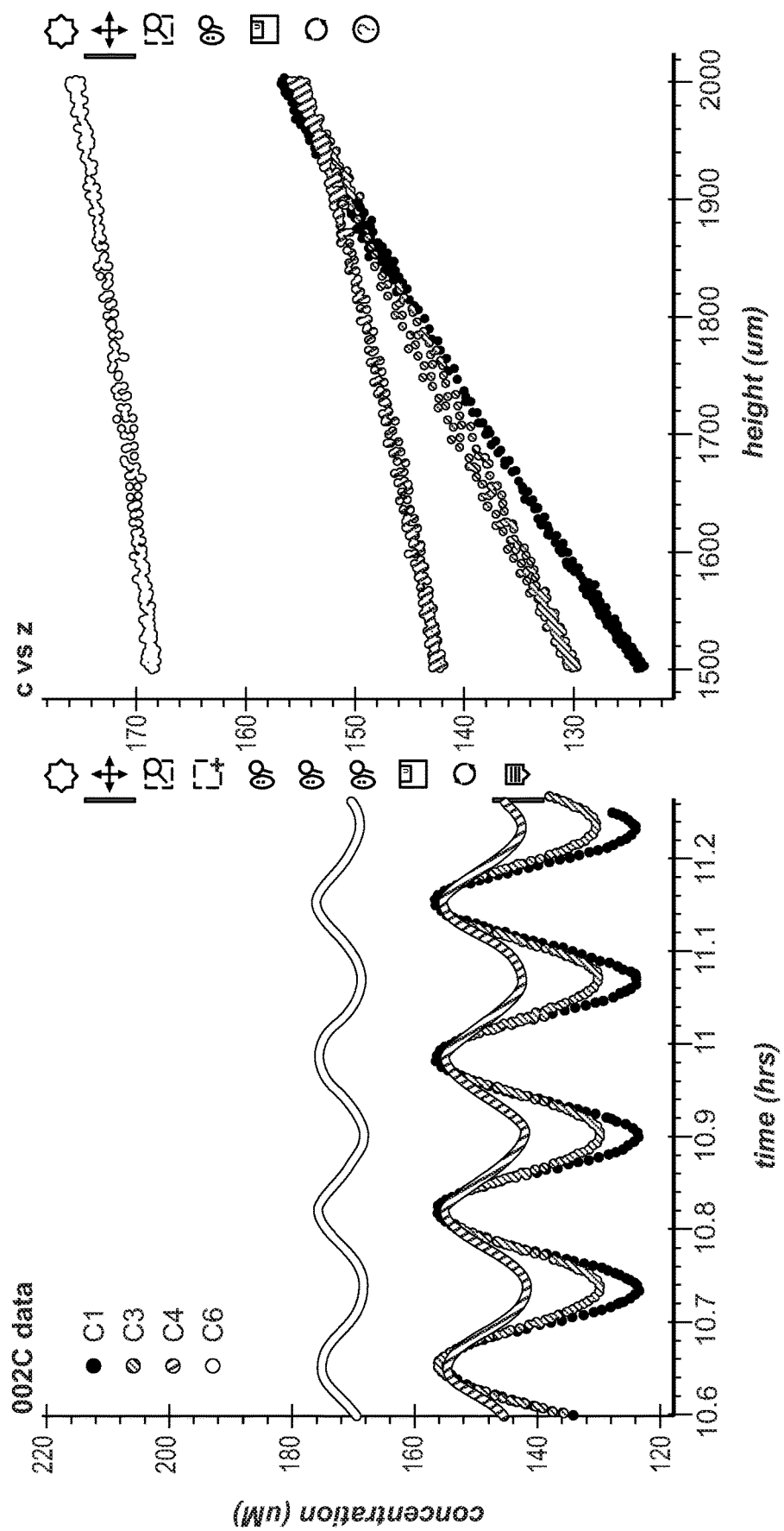

As shown in FIG. 11B, after the sensor response is compensated for, the concentration readings in steady state gradients are a linear function of height. This is in agreement with expectations for the diffusion gradient formed with steady-state flux (i.e., cellular oxygen consumption) at the bottom of a well with stable atmospheric conditions at the top surface. These values can now be used to evaluate concentration estimates at a set uniform, discrete heights to produce a Kalman observation for input into the Kalman filter. An example linear interpolation with a small set of heights is shown in the figure. This interpolation step enables the use of a Kalman state with fewer concentration values while still using sensor readings at arbitrary points within the movement pattern.

3.3.4 Kalman Filter State

The Kalman filter state consists of a set of concentrations at uniformly-spaced relative heights, $c_0 \ldots c_{N-1}$, a bottom flux to/from the cells, $q_c$, and a top flux, $q_t$. The state update can be computed according to Fick's law using finite differences.

For example, the state x with N height concentrations would be:

$$x^T = [q_t c_{N-1} \ldots c_1 c_0 q_c]$$

3.3.5 Kalman State Transition Model

The Kalman state transition updates can be can be computed, in some embodiments, based at least in part on Fick's law for the modeled well environment.

3.3.6 Output Measurements

The primary measurement parameter output of the system is the Kalman estimate of flux $q_c$ as this directly relates to cell activity and can be further processed into specific measurements of cell activity such as oxygen consumption rate. In addition to this, the other state variables of the Kalman Filter can all be used as output measurement estimates. Higher-level measures and events may be inferred from these measurements as well. If the concentration estimate as a function of height match a specific shape, then a non-uniform cell seeding density may be inferred. Additionally, if a low, but increasing, gradient is detected across many or all wells, a media change event could be inferred. These events can automatically trigger a movement pattern change as described elsewhere.

In general, when oxygen consumption by the cells is uniform, at steady state the gradient in the well reduces to a uniform, one-dimensional, linear gradient. This is assuming a uniform cell density as well. When consumption is higher directly below the path of the probe the gradient is higher towards the bottom of the well and lower towards the top of the well, thus creating an upward curved gradient along the path of the probe. The opposite is true when consumption is higher away from the probe than directly underneath the probe, and the gradient along the path of the probe curves downward. Using this information, the system can inform the user of uneven cell distribution within the wells, or can inform the user of an expected bulk consumption measurement or range of measurements across the well surface.

In other embodiments, a non-linear spatio temporal model (for example a non-linear autoregressive moving average model with exogenous inputs or NARMAX model) is employed (see, e.g., Stephen A. Billings. *Nonlinear system identification: NARMAX methods in the time, frequency, and spatio-temporal domains*. Wiley, September 2013. ISBN 978-1-119-94359-4.) In this scenario, both current probe position and concentration readings are fed into a non-linear model as inputs, and the model is used to estimate parameters of the underlying system including transport of the molecule of interest through the region of interest.

4 Data Handling

4.1 Software

The measurement system includes a computing subsystem that can be configured to execute multiple software components that are able to perform a variety of useful operations. These components include embedded software running on circuitry within the device and, in some embodiments, coupled to the optoelectronic sensor array (see section under Disposable Probe Lid), data processing and storage software, and user interface software for data visualization, device control, and general lab experiment features.

4.1.1 Software for Lid Integration

In some embodiments, the software installed on an embedded device (e.g., a processor or other computing circuitry) within the device, and coupled to the optoelectronic sensor array, includes functionality for any of the following:
reading the optical sensors
reading the auxiliary sensors (temperature, humidity, accelerometer, atmospheric pressure, ambient light, etc.)
actuation control in order to perform the movement pattern
lid attachment detection
lid data read/write
lid data validation and authentication
communication interface with data processing and storage system

4.1.2 Data Processing and Storage

Additional processing and storage of the data generated by the embedded device may be performed by software running on a coupled secondary system. This software may be run on a desktop, a server, or embedded OS, for example. This software can be distributed across hardware components and may either reside locally to the measurement environment or remotely (i.e., via communication with 'cloud' software). This software can store the data measurements to a database for later analysis. The software can forward the data to user interface software for real-time visualization and monitoring. This software can also communicate with the device in various ways and may rely on a variety of protocols including USB, bluetooth, TCP/IP, WiFi, etc. Furthermore, the software can perform data backups for redundant storage and data recovery.

4.1.3 User Interface

The system can be monitored and controlled via a user interface managed by software configured to render the user interface on a display and configured to receive input over one or more input devices. This software may reside on the same system as the data processing and storage software or on a separate hardware device such as touchscreen tablet or workstation. This software can be a traditional desktop application, a web application, a mobile application, or a combination thereof. It can provide visualizations of the system measurements provided to the user. The software can enable the control of device operation and configuration of various system parameters.

The software can also include general features useful for performing an experiment, including logging of experiment start time, end time, summary, notes, events, conditions, etc.

The software can also display results, or representations of results aggregated from previous experiments for comparison with an experiment as the experiment occurs in real-time. These results from previous experiments can be from experiments performed with the same device, or they can be results from experiments performed on other devices or from other laboratories. These previous results can be displayed exactly as is, or they can be aggregated and scaled using a variety of techniques.

4.1.4 Experiment Authentication

The system software can also provide experiment authenticity capabilities for audit and verification of lab experiments. Fabrication, falsification, and plagiarism of scientific data is a significant problem. By using a digital signature algorithm (e.g. ECDSA) and optionally on-board tamper proof components, the system can help to ensure the following for a given experiment:
data integrity—data was not modified (secure on-board digital signatures)
attribution—data was recorded by a specific device (secure on-board signatures)
data was recorded at a certain date and time (on-board tamper proof clock)
data was recorded at a certain location (on-board tamper proof GPS)
good laboratory practice (GLP) compliance

5 Example Measurement Data

Figure 9:
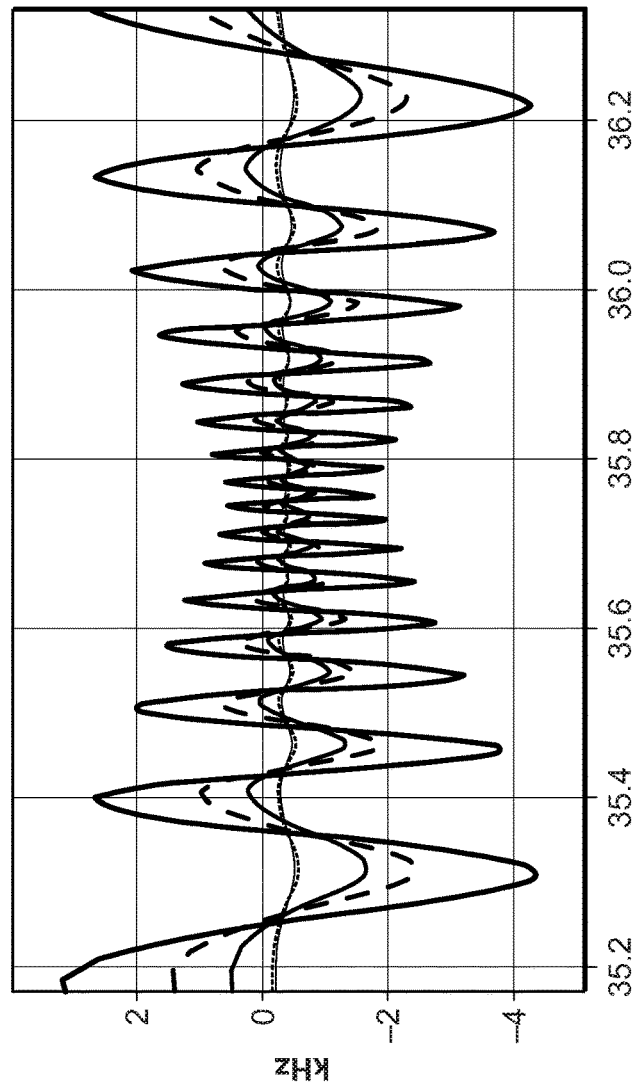
FIGS. 9, 10A, 10B, 11A, 11B, 12A, and 12B are plots of example measurements corresponding to different embodiments of the measurement system.

FIG. 9 shows an example of mean-centered measurements (uncalibrated) from 4 sensors using an exponential chirp movement pattern for just over an hour. Since the sensors are operating in a steady state linear gradient and the amplitude of the chirp movement pattern is constant, the change in amplitude of the readings indicates a frequency-dependent attenuation in the readings that can be modeled as an LTI filter or other system transfer function acting on the movement pattern signal. Note: y-axis is time in experiment hours.

Figures 10A, 10B:
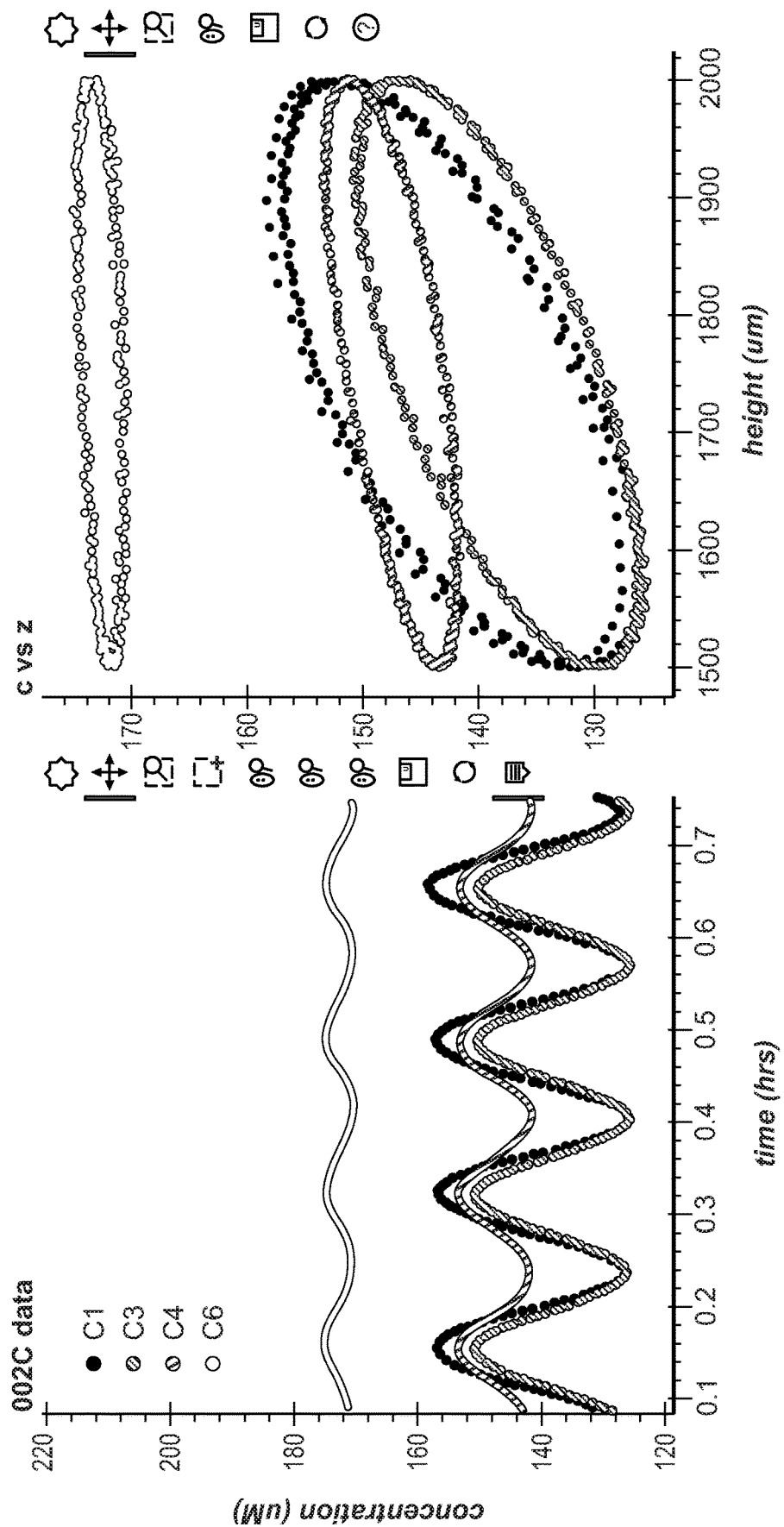

FIGS. 10A and 10B show an example of concentration measurements (FIG. 10A) from 4 sensors using a sinusoidal movement pattern and (FIG. 10B) these concentration values as a function of probe depth at the time of reading without compensating for sensor response (sensor lag) in the readings relative to the cycle pattern. The data undergo further processing since the concentration vs. height profile is not consistent with the profile expected based on the laws of diffusion.

FIGS. 11A and 11B show an example of concentration measurements (FIG. 11A) from 4 sensors using a sinusoidal movement pattern and (FIG. 11B) these concentration values as a function of probe height after compensating for an approximate 80 second lag in the readings relative to the cycle pattern. After compensation, the concentration vs. height profile appears linear in accordance with a steady state linear gradient.

Figure 12B:
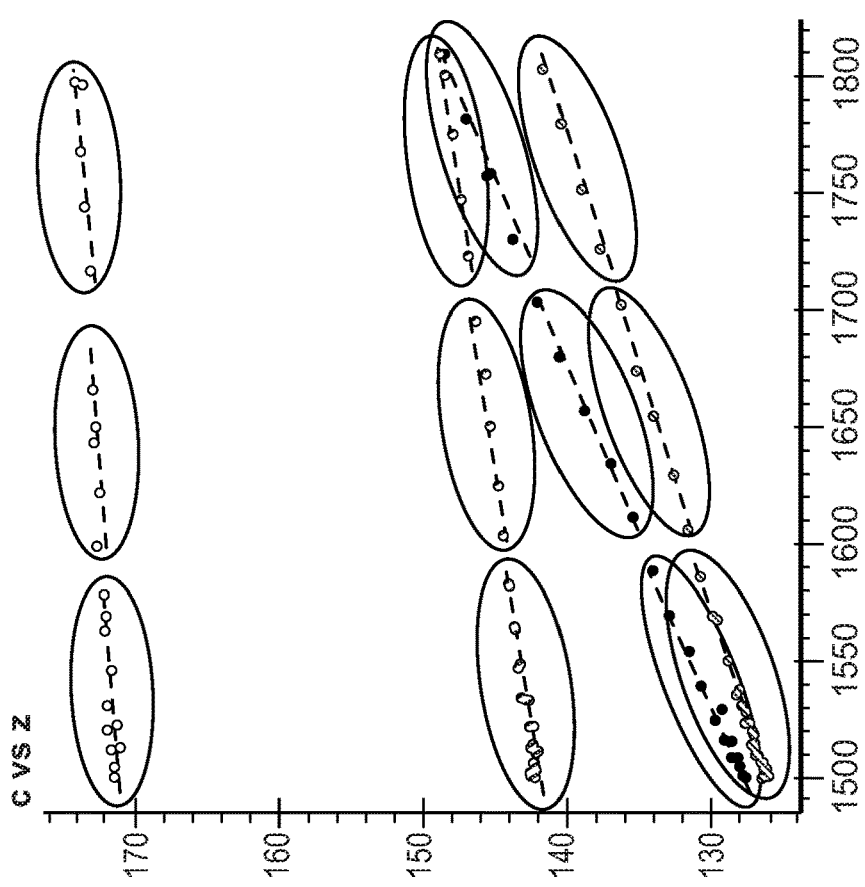
Figure 12A:
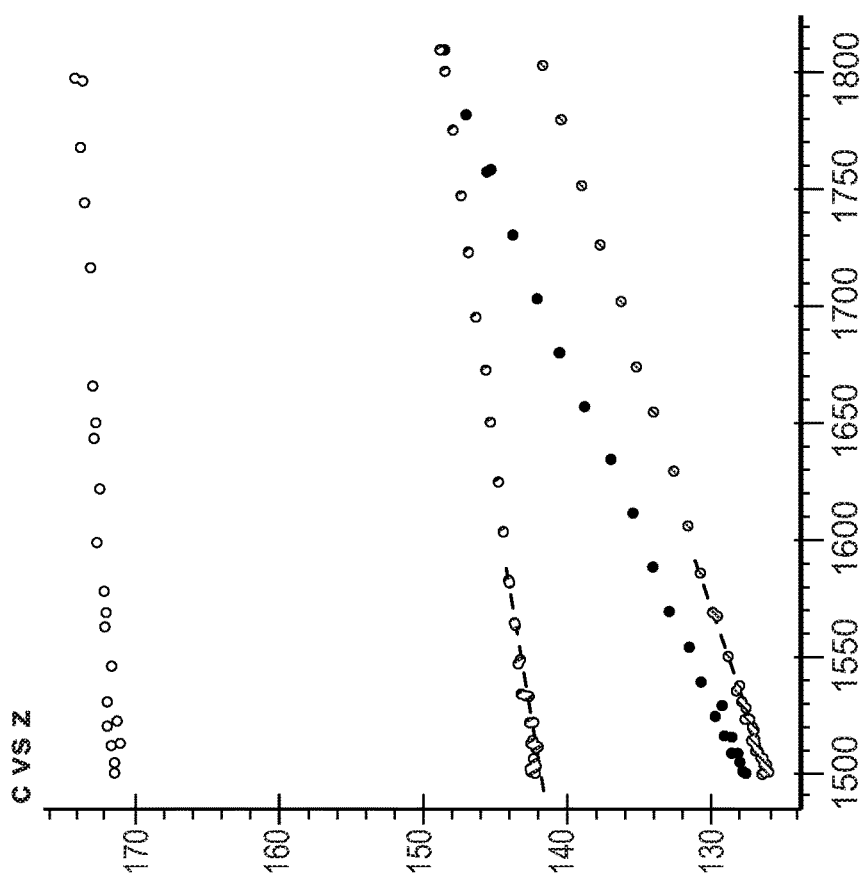

FIGS. 12A and 12B show an example conversion from a set of lag-compensated concentration values for 4 sensors to Kalman Observations for a N=3 height model. The bubbles represent the cluster of values used for regression and interpolation at each of the three heights. The dashed line represents the linear regression for each cluster. The concentration estimates ($c_1$, $c_2$, $c_3$) at each height are then interpolated for updating the Kalman state. The slope of these lines (dC/dz) can also be used to estimate the degree of non-linearity of the entire profile—which may indicate either a rapidly changing flux or an uneven consumption distribution (i.e., non-uniform cell density). Note: x-axis is probe height above well bottom in micrometers, y-axis is oxygen concentration in micromolar.

6 Alternatives and Implementations

A number of alternatives to the embodiments described may be used. For example, although the probes are caused to move relative to the wells, for example, to sense an oxygen gradient at various depths, in some alternatives, it is the receptacle that moves relative to a fixed reference (e.g., a shelf in an incubator) rather than the receptacle remaining fixed, and the probes moving, for example, with the movement of the device or some other cover.

A number of embodiments use standard culture trays with arrays of 6, 12, 96, etc. wells. In an alternative, a single well receptacle, such as a cell culture flask may be used, and there may be one or more typically multiple probes into the single well.

The techniques described above can be implemented using a program comprising instructions for execution on a device or module (e.g., the control module and/or analysis module) including one or more processors or other circuitry for executing the instructions. For example, the instructions execute procedures of software or firmware that runs on one or more programmed or programmable computing devices or modules including at least one processor and at least one data storage system (e.g., including volatile and non-volatile memory, and/or storage media). The programs may be provided on any non-transitory medium, including a computer-readable storage medium, such as a CD-ROM, readable by a general or special purpose programmable computer, or delivered over a communication medium such as network to a computer where it is executed. Each such program may be stored on or downloaded to a storage medium (e.g., solid state memory or media, or magnetic or optical media) readable by a computing device, for configuring and operating the device when the storage medium is read by the device to perform the procedures of the program.

It is to be understood that the foregoing description is intended to illustrate and not to limit the scope of the invention, which includes the scope of the appended claims. Other embodiments are within the scope of the following claims.

What is claimed is:

1. An apparatus for measurement of molecule levels in fluid in a receptacle, the apparatus comprising:
 a device configured to be attached as part of a cover over a receptacle having a set of wells for holding a biological sample immersed in fluid, wherein the device comprises:
 a plurality of optoelectronic sensors arranged to acquire optical signals from respective probes immersed in the fluid, each optical signal representing a molecule level in fluid at a respective probe;
 a set of actuators configurable to adjust a relative position of the device and the receptacle; and
 control circuitry configured to control the set of actuators to vary the relative position of the device and the receptacle, and to acquire the optical signals at a plurality of relative positions; and
 a lid configured to be attached to the device to form the cover, the lid comprising:
 a surface configured to cover the wells of the receptacle; and
 a set of probes, such that each probe extends substantially perpendicularly from the surface of the lid;
 wherein the lid is configured such that a location of each probe of the lid corresponds to a location of an optoelectronic sensor of the device such that, when the lid is attached to the device, an optical path is formed between a sensor of the probe and a corresponding optoelectronic sensor;
 wherein the lid is further configured such that the location of each probe of the lid corresponds to a position within a well of the set of wells of the receptacle;
 wherein, when the apparatus is attached as part of the cover over the receptacle, varying the relative position of the device and the receptacle causes variation of depth of the probes in the fluid of the wells; and
 wherein the device is configured to rest on top of the lid and be fully supported by the lid and the receptacle.

2. The apparatus of claim 1 wherein the device includes a plurality of actuators, wherein the plurality of actuators are jointly controllable by the control circuitry to control an orientation of a plane defined by the sensors of the probes relative to a plane defined by the set of wells of the receptacle.

3. The apparatus of claim 1 wherein the control circuitry is configured to maintain a plane defined by the sensors of the probes and a plane defined by the set of wells of the receptacle to be parallel.

4. The apparatus of claim 1 wherein the varying of the relative position of the device and the receptacle is over a range of motion, and range of motion is between 10 micrometers and 3 millimeters.

5. The apparatus of claim 1 wherein the lid comprises a sterile material.

6. The apparatus of claim 1 wherein the lid is configured to, when attached to a receptacle, separate surfaces of the device from the wells, thereby maintaining a sterile environment in the wells.

7. The apparatus of claim 1 wherein the lid is configured to form to cover the wells maintaining a gas path between the wells and an environment outside the apparatus and maintaining a sterile barrier between the well and the environment.

8. The apparatus of claim 7 wherein the lid is configured to form tortuous paths between the wells and the environment without forming any straight-line path from in or above any well and the environment.

9. The apparatus of claim 1 wherein the lid comprises a set of flexure portions, each flexure portion having greater flexibility than other portions of the lid such that in movement over the varying relative position of the device relative to the receptacle, at least a first portion of the lid remains in contact with the receptable and at least a second portion of the lid, separated from the first portion by the flexure portion, remains in contact with the device.

10. The apparatus of claim 9 wherein the set of flexure portions form a spring having a force such that a weight of the device is sufficient to compress the flexure portions over the varying relative position of the device and the receptacle, and the spring applies sufficient force to maintain contact of the lid with the device over the varying relative position.

11. The apparatus of claim 1 wherein the cover formed from the device and the lid is configured to be removable from the receptacle without moving the receptacle.

12. The apparatus of claim 1 wherein the lid includes guide elements for engaging with corresponding elements of the device to fix a relative position of the lid and the device.

13. The apparatus of claim 12 wherein the guide elements include at least one of a protrusion and an indentation in a surface of the device.

14. The apparatus of claim 1 wherein lid is translucent.

15. The apparatus of claim 1 wherein lid is sterile.

16. The apparatus of claim 1 wherein lid comprises a set of fluid dispensing ports, each of said ports being configured to dispense a fluid stored in the lid into a corresponding well.

17. The apparatus of claim 1 wherein the device has a mass of less than 1000 grams.

18. The apparatus of claim 17 wherein the device has a mass of less than 250 grams.

19. The apparatus of claim 1 wherein the lid is fixedly attached to the device maintaining alignment of the probes of the lid and the optoelectronic sensors of the device over a range of motion of the varying relative position.

20. The apparatus of claim 1 wherein the device includes a data interface for receiving data from a corresponding element in the lid.

21. The apparatus of claim 20 wherein the data interface comprises electric contacts for electrically connecting to corresponding electrical contacts of the corresponding element of the lid.

22. The apparatus of claim 20 wherein the data interface comprises an imaging sensor for acquiring an image of a portion of a surface of the lid.

23. The apparatus of claim 20 wherein the data interface comprises a radio frequency communication device.

24. The apparatus of claim 20 wherein the data interface is coupled to the control circuitry for controlling the actuators and acquisition of the optical signals from the sensors.

25. The apparatus of claim 1 wherein the apparatus further comprises the receptacle, wherein the lid is attached to the device and disposed between the device and the receptacle maintaining a sterile barrier between the surface of the fluid and the environment and there is at least some gas path between each well and the environment.

26. The apparatus of claim 25 wherein the receptacle comprises a plurality of wells, and the lid is configured with at least one probe corresponding to each well.

27. The apparatus of claim 25 wherein the lid is configured with multiple probes corresponding to the single well.

28. The apparatus of claim 1 further comprising a data processing system configured to accept data representing sensor values acquired at multiple relative positions.

29. The apparatus of claim 28 wherein the data processing system is configured to combine the accepted data to compute a consumption rate of the molecule by the biological sample.

30. The apparatus of claim 28 wherein the data processing system comprises a display for displaying quantities derived from the sensor values.

31. The apparatus of claim 30 wherein the data processing system is configured to display the quantities derived from the sensor values in combination with reference quantities.

32. The apparatus of claim 1 wherein the molecule comprises oxygen.

33. The apparatus of claim 1, wherein the control circuitry configured to control the set of actuators is configured to continuously vary depths of probes within fluid in the receptacle and to acquire a plurality of optical signals while continuously moving the probes.

34. The apparatus of claim 33, wherein the control circuitry is configured to move the probes within the receptacle according to at least one pattern from a set of patterns consisting of sinusoids, multiple sinusoids at different frequencies, sawtooth, sinc, chirp, and irregular patterns.

35. The apparatus of claim 1, wherein each probe of these set of probes comprises an elongated light guide for passing acquired light from a tip of the probe immersed in the fluid to an optoelectronic sensor of a device attached to the lid.

36. The apparatus of claim 1, wherein the lid is configured to fully support the device resting on top of the lid.

37. The apparatus of claim 1, wherein the lid is configured to enable the device to cause relative movement between the lid and receptacle without requiring the device to directly interface the receptacle.

38. The apparatus of claim 1, wherein a location of each probe of the lid aligns with a location of a corresponding optoelectronic sensor of the device.

39. The apparatus of claim 1, wherein the device further comprises circuitry for passing signals from the optoelectronic sensors of the device forming the cover to an external processing system.

40. The apparatus of claim 1, wherein the device is configured to be handheld.

41. An apparatus for measurement of a molecule levels in fluid in a receptacle, the apparatus including a device configured to be attached as part of a cover comprising a plurality of probes over a receptacle having a set of wells for holding a biological sample immersed in fluid such that varying a relative position of the device and the receptacle causes variation of depth of the probes in the fluid of the wells, wherein the device includes:
   a plurality of optoelectronic sensors arranged to acquire optical signals from respective probes immersed in the fluid, each optical signal representing a molecule level in fluid at a respective probe;
   a set of actuators configurable to adjust the relative position of the device and the receptacle; and
   control circuitry configured to control the set of actuators to vary the relative position of the device relative to the receptacle, and while varying the relative position to acquire the optical signals in the receptacle at a plurality of respective positions of the device relative to the receptacle, wherein the control circuitry is configured to operate when the device is attached as part of the cover over the receptacle to
   cause relative movement between the receptacle and the plurality of probes, the relative movement being performed over a measurement interval comprising multiple time periods, where a distance between the receptacle and the array of probes both increases and decreases along a first axis over at least a portion of each time period, wherein:
      each probe is configured to measure the molecule level within the fluid, at a distance from the bottom surface of a well that depends on the distance between the receptacle and the probes, and the relative movement is along the first axis substantially perpendicular to the plane of the top surface of the fluid; and acquire measurement data from two or more of the plurality of probes, over each of a plurality of the time periods, wherein, for at least a first probe configured to measure a concentration of the molecule within the fluid contained in a first well of the set of wells, wherein:

measurement data acquired from the first probe includes at least two data samples acquired at different respective positions in the first well within a first time period of the plurality of the time periods.

42. The apparatus of claim 41, wherein the control circuitry is configured to vary speed of the movement within each time period.

43. The apparatus of claim 41, wherein the control circuitry is configured to vary movement patterns between time periods.

* * * * *